(12) United States Patent
Oki

(10) Patent No.: US 12,232,812 B2
(45) Date of Patent: Feb. 25, 2025

(54) FUNDUS CAMERA AND CONTROL METHOD OF THE SAME

(71) Applicant: Topcon Corporation, Tokyo (JP)

(72) Inventor: Takuya Oki, Tokyo (JP)

(73) Assignee: Topcon Corporation, Tokyo (JP)

( * ) Notice: Subject to any disclaimer, the term of this patent is extended or adjusted under 35 U.S.C. 154(b) by 644 days.

(21) Appl. No.: 17/393,412

(22) Filed: Aug. 4, 2021

(65) Prior Publication Data

US 2022/0087525 A1 Mar. 24, 2022

(30) Foreign Application Priority Data

Sep. 24, 2020 (JP) ................................ 2020-159690

(51) Int. Cl.
| | |
|---|---|
| *A61B 3/10* | (2006.01) |
| *A61B 3/00* | (2006.01) |
| *A61B 3/02* | (2006.01) |
| *A61B 3/11* | (2006.01) |
| *A61B 3/12* | (2006.01) |

(52) U.S. Cl.
CPC .............. *A61B 3/12* (2013.01); *A61B 3/0008* (2013.01); *A61B 3/112* (2013.01)

(58) Field of Classification Search
CPC ......... A61B 3/02; A61B 3/1025; A61B 3/102; A61B 3/113; A61B 3/1015; A61B 3/1225
USPC ....... 351/206, 200, 205, 209, 210, 221, 222, 351/246
See application file for complete search history.

(56) References Cited

U.S. PATENT DOCUMENTS

| | | |
|---|---|---|
| 2010/0057059 A1 | 3/2010 | Makino |
| 2012/0224141 A1 | 9/2012 | Ichikawa et al. |
| 2013/0208243 A1 | 8/2013 | Sakagawa |

(Continued)

FOREIGN PATENT DOCUMENTS

| | | |
|---|---|---|
| DE | 10 2015 001 313 A1 | 8/2016 |
| EP | 2138093 B1 | 5/2011 |

(Continued)

OTHER PUBLICATIONS

Extended European search report issued on Feb. 15, 2022, in corresponding European patent Application No. 21192787.6, 25 pages.

(Continued)

*Primary Examiner* — Dawayne Pinkney
(74) *Attorney, Agent, or Firm* — XSENUS LLP

(57) ABSTRACT

A fundus camera for reliably performing fundus imaging in a state where no miosis has been caused in the pupil of a subject eye, and a corresponding method. The fundus camera includes a camera main body configured to image the fundus of a subject eye, an anterior ocular segment image acquiring unit configured to repeatedly acquire an anterior ocular segment image of the subject eye at least before the imaging of the fundus by the camera main body, a pupil diameter detecting unit configured to repeatedly detect the pupil diameter of the subject eye based on the anterior ocular segment image repeatedly acquired by the anterior ocular segment image acquiring unit, and an imaging control unit configured to cause the camera main body to image the fundus in a case where the pupil diameter detected by the pupil diameter detecting unit reaches a predetermined first threshold value or more.

11 Claims, 17 Drawing Sheets

(56) References Cited

U.S. PATENT DOCUMENTS

| | | |
|---|---|---|
| 2013/0208244 A1 | 8/2013 | Sakagawa |
| 2014/0300864 A1 | 10/2014 | Fukuma et al. |
| 2015/0085252 A1 | 3/2015 | Fujimura et al. |
| 2015/0313468 A1* | 11/2015 | Okada .................. A61B 3/113 351/208 |
| 2016/0120405 A1 | 5/2016 | Tokuda et al. |
| 2019/0090736 A1 | 3/2019 | Nakajima |
| 2020/0196863 A1* | 6/2020 | Anderson ............ A61B 3/0025 |
| 2021/0307604 A1 | 10/2021 | Matsumura et al. |

FOREIGN PATENT DOCUMENTS

| | | |
|---|---|---|
| EP | 2786698 B1 | 11/2015 |
| JP | 5-199997 A | 8/1993 |
| JP | 2009-112664 A | 5/2009 |
| JP | 2012-179205 A | 9/2012 |
| JP | 2013-165819 A | 8/2013 |
| JP | 2013-248376 A | 12/2013 |
| JP | 2014-226370 A | 12/2014 |
| JP | 2015-177881 A | 10/2015 |
| JP | 2019-62982 A | 4/2019 |
| JP | 2019-171221 A | 10/2019 |
| KR | 10-2020-0069547 A | 6/2020 |
| WO | 2014/091992 A1 | 6/2014 |
| WO | 2020/032128 A1 | 2/2020 |

OTHER PUBLICATIONS

Eileen E. Birch et al., "Pupillometric Measures of Retinal Sensitivity in Infants and Adults With Retinitis Pigmentosa", Vision Research, vol. 27, No. 4, pp. 499-505, 1987.

Japanese Office Action issued Nov. 1, 2024, in corresponding Japanese Patent Application No. 2020-159690, 12 pp.

* cited by examiner

FUNDUS CAMERA AND CONTROL METHOD OF THE SAME

CROSS-REFERENCE TO RELATED APPLICATION

The present application claims priority under 35 U.S.C § 119 to Japanese Patent Application No. 2020-159690 filed on Sep. 24, 2020. The above application is hereby expressly incorporated by reference, in its entirety, into the present application.

BACKGROUND OF THE INVENTION

Field of the Invention

The present invention relates to a fundus camera (retinal camera) for imaging a fundus of a subject eye (eye to be examined), and a control method for the same.

Description of the Related Art

A fundus camera for taking an image of a fundus of a subject eye is well known (see Japanese Patent Application Laid-Open No. 2019-171221, Japanese Patent Application Laid-Open No. H5-199997, and Japanese Patent Application Laid-Open No. 2013-248376). The fundus camera illuminates a fundus of a subject eye with observation illumination light (flash light or the like), and takes an image of the fundus illuminated with the observation illumination light. Examples of known methods for taking an image of the fundus of an eye by using the fundus camera include: a sequential imaging method for sequentially performing a plurality of imaging operations on the same subject eye; and a right-and-left eye imaging method for performing an imaging operation on the fundus of each of the right and left eyes in turn.

CITATION LIST

Patent Literature 1: Japanese Patent Application Laid-Open No. 2019-171221
Patent Literature 2: Japanese Patent Application Laid-Open No. H5-199997
Patent Literature 3: Japanese Patent Application Laid-Open No. 2013-248376

SUMMARY OF THE INVENTION

Observation illumination light (flash light or the like) is emitted from a fundus camera to the fundus of an eye during imaging of the fundus of a subject eye. The observation illumination light includes light in the visible wavelength band, and the quantity of the light in the visible wavelength band is large. For this reason, in a case where non-mydriatic fundus imaging is performed for a subject eye, the subject eye is irradiated with observation illumination light from the fundus camera during the fundus imaging, which causes miosis of the pupil of the subject eye, and it takes time until the miosis of the pupil is settled (the diameter of the pupil is returned to its original diameter). Therefore, when the sequential imaging is performed by using the fundus camera in each of the above-described patent literatures, the miosis of the pupil has not yet been settled in the second and subsequent fundus imaging operations on the subject eye, and thus there is a risk that no satisfactory fundus image can be obtained.

Further, the diameters of the pupils of the right and left eyes change equally. Therefore, when the right-and-left eye imaging is performed by using the fundus camera described in each of the above-described patent literatures, that is, when the fundus imaging is performed on one of the right and left eyes and then the fundus imaging is sequentially performed on the other eye of the right and left eyes, there is a risk that the miosis of the pupil of the other eye has not yet been settled. Further, when a subject eye has been irradiated with illumination light by another ophthalmologic apparatus before the fundus imaging is performed on the subject eye by the fundus camera, there is a risk that the miosis of the pupil of the subject eye has not yet been settled in spite of the first fundus imaging operation on the subject eye by the fundus camera, so that no satisfactory fundus image may be obtained.

The present invention has been made in view of such circumstances, and aims to provide a fundus camera which can reliably perform fundus imaging in a state where no miosis is caused in the pupil of a subject eye, and a control method of the same.

In order to attain the object of the present invention, a fundus camera according to an aspect of the present invention comprises: a camera main body configured to image a fundus of a subject eye; an anterior ocular segment image acquiring unit configured to repeatedly acquire an anterior ocular segment image of the subject eye at least before the fundus is imaged by the camera main body; a pupil diameter detecting unit configured to repeatedly detect a pupil diameter of the subject eye based on the anterior ocular segment image repeatedly acquired by the anterior ocular segment image acquiring unit; and an imaging control unit configured to cause the camera main body to image the fundus in a case where the pupil diameter detected by the pupil diameter detecting unit reaches a predetermined first threshold value or more.

According to the fundus camera, it is possible to suspend performing fundus imaging until the pupil diameter of the subject eye reaches the first threshold value or more, and perform the fundus imaging when the pupil diameter reaches the first threshold value or more.

In the fundus camera according to another aspect of the present invention, the camera main body includes an illumination optical system configured to illuminate the fundus with imaging illumination light in a visible wavelength band when the camera main body images the fundus, and perform first imaging on the fundus and second imaging subsequent to the first imaging, and the imaging control unit suspends execution of the second imaging by the camera main body until the pupil diameter reaches the first threshold value or more based on a detection result of the pupil diameter repeatedly detected by the pupil diameter detecting unit after the first imaging and before start of the second imaging, and causes the camera main body to perform the second imaging when the pupil diameter reaches the first threshold value or more. As a result, even in a case where miosis is caused in the pupil of the subject eye due to the first imaging, the second imaging can be automatically performed at a time point when the miosis has been settled.

The fundus camera according to another aspect of the present invention further comprises a threshold value determining unit configured to determine the first threshold value based on the pupil diameter detected by the pupil diameter detecting unit before the first imaging, and the imaging control unit causes the camera main body to perform the second imaging when the pupil diameter detected by the pupil diameter detecting unit reaches the first threshold value determined by the threshold value determining unit or more. As a result, even in a case where there are individual differences in the pupil diameters for respective subjects, a first threshold value corresponding to each of the subjects can be individually determined.

In the fundus camera according to another aspect of the present invention, the camera main body performs the first imaging and the second imaging on the same subject eye.

In the fundus camera according to another aspect of the present invention, when the subject eye is either of right and left eyes, the camera main body performs the first imaging on one of the right and left eyes, and performs the second imaging on the other eye of the right and left eyes.

The fundus camera according to another aspect of the present invention further comprises: a small pupil diaphragm provided so as to be arrangeable on an optical path of the illumination optical system, and adapted to a small pupil eye; and a first special imaging control unit configured to cause the camera main body to image the fundus in a state where the small pupil diaphragm is arranged on the optical path when the pupil diameter is less than the first threshold value even after a lapse of a certain predetermined time, based on the pupil diameter repeatedly detected by the pupil diameter detecting unit after the first imaging and before start of the second imaging. As a result, a fundus image can be captured in a short time.

The fundus camera according to another aspect of the present invention further comprises: a time predicting unit configured to predict a return time required until the pupil diameter increases up to the first threshold value, based on a detection result by the pupil diameter detecting unit when the camera main body has performed the first imaging; and a notifying unit configured to notify the return time predicted by the time predicting unit. As a result, an operator can recognize the return time, that is, a timing at which the second imaging is to be started.

In the fundus camera according to another aspect of the present invention, the time predicting unit predicts the return time based on the detection result by the pupil diameter detecting unit and a type of the imaging illumination light.

In the fundus camera according to another aspect of the present invention, the time predicting unit detects a change in the pupil diameter after the first imaging is performed based on the pupil diameter repeatedly detected by the pupil diameter detecting unit, and calculates the return time based on a detection result of the change in the pupil diameter.

In the fundus camera according to another aspect of the present invention, the camera main body includes an illumination optical system configured to illuminate the fundus with imaging illumination light in a visible wavelength band, and the fundus camera further comprises: a small pupil diaphragm provided so as to be arrangeable on an optical path of the illumination optical system and adapted to the small pupil eye; and a second special imaging control unit configured to cause the camera main body to image the fundus in a state where the small pupil diaphragm is arranged on the optical path in a case where the small pupil diameter determining unit determines that the subject eye is the small pupil eye. As a result, when the subject eye is a small pupil eye, the small pupil diaphragm can be automatically arranged on the optical path of the illumination light.

In the fundus camera according to another aspect of the present invention, the small pupil diameter determining unit determines whether the subject eye is a small pupil eye based on whether the pupil diameter detected by the pupil diameter detecting unit is less than a predetermined second threshold value which is smaller than the first threshold value.

In order to attain the object of the present invention, a control method of a fundus camera for imaging a fundus of a subject eye comprises: an anterior ocular segment image acquiring step of repeatedly acquiring an anterior ocular segment image of the subject eye at least before the fundus is imaged; a pupil diameter detecting step of repeatedly detecting a pupil diameter of the subject eye based on the anterior ocular segment image that is repeatedly acquired in the anterior ocular segment image acquiring step; and an imaging control step of imaging the fundus when the pupil diameter detected in the pupil diameter detecting step reaches a predetermined first threshold value or more.

According to the present invention, it is possible to reliably perform fundus imaging in a state where no miosis has been caused in the pupil of a subject eye.

DETAILED DESCRIPTION OF THE PREFERRED EMBODIMENTS

[Overall Configuration of Ophthalmologic Apparatus of First Embodiment]

Figure 1:
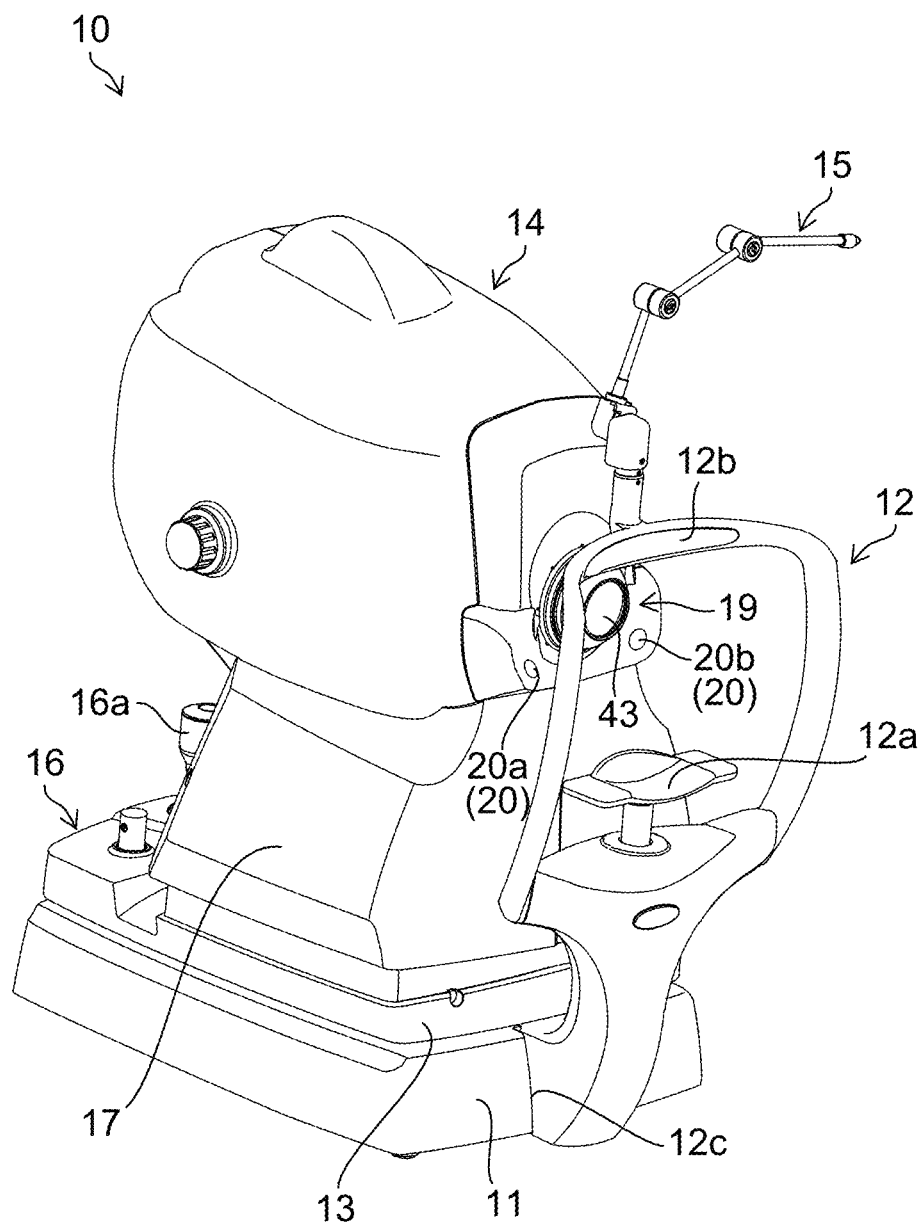
FIG. 1 is a front perspective view of an ophthalmologic apparatus according to a first embodiment as viewed from a subject side.
Figure 1:
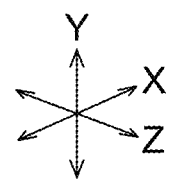
Figure 2:
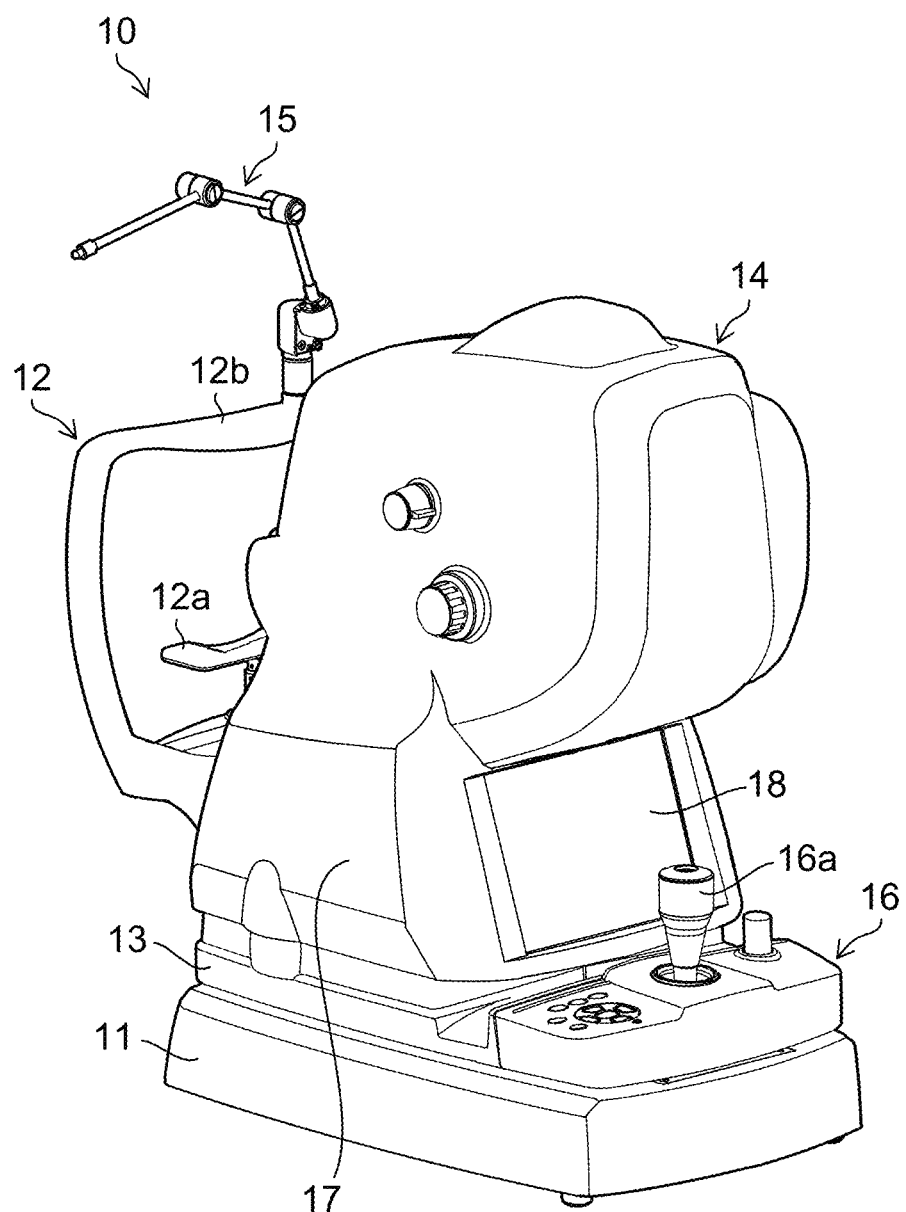
FIG. 2 is a rear perspective view of the ophthalmologic apparatus as viewed from an operator side.
Figure 2:
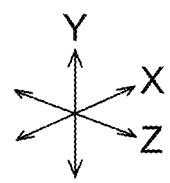

FIG. 1 is a front perspective view of an ophthalmologic apparatus 10 of a first embodiment as viewed from a subject side. FIG. 2 is a rear perspective view of the ophthalmologic apparatus 10 as viewed from an operator side. Note that an X direction and a Y direction in FIGS. 1 and 2 are a right-and-left direction (an eye-width direction of an eye E under examination shown in FIG. 3) and an up-and-down (vertical) direction with respect to a subject respectively, and a Z-direction is a front-and-back direction (also called s working distance direction) which is parallel to a forward direction approaching to the subject and a backward direction away from the subject.

As shown in FIGS. 1 and 2, the ophthalmologic apparatus 10 is a composite machine combining a fundus camera (non-mydriatic fundus camera) and an optical coherence tomography meter for acquiring an OCT image as a tomographic image by using an optical coherence tomography (OCT).

The ophthalmologic apparatus 10 performs fundus imaging for taking an image of the fundus Ef (see FIG. 3) of a subject eye E (see FIG. 3) under non-mydriasis, and also performs OCT measurement for obtaining an OCT image of the fundus Ef of the subject eye E. Further, the ophthalmologic apparatus 10 has a sequential imaging mode and a right-and-left eye imaging mode, as imaging modes for performing fundus imaging of the subject eye E, in addition to a normal imaging mode in which fundus imaging is performed only once. The sequential imaging mode is a mode in which a plurality of fundus imaging operations are sequentially performed on the same subject eye E. The right-and-left eye imaging mode is a mode in which a fundus imaging operation is performed on right and left subject eyes E (right and left eyes) in turn.

The ophthalmologic apparatus 10 includes a base 11, a face supporting part 12, a pedestal 13, and a measuring head 14.

The face supporting part 12 and the pedestal 13 are mounted on the base 11.

The face supporting part 12 is provided integrally with the base 11 at a position on the front side of the measuring head 14 in the Z direction. The face supporting part 12 includes a jaw holder 12a and a forehead pad 12b which can be positionally adjusted in the Y direction (up-and-down direction), and supports the subject's face at a position where the subject's face faces an ophthalmologic apparatus main body such as the measuring head 14 (objective lens 43 described later).

The face supporting part 12 is provided with an external fixation lamp 15. The external fixation lamp 15 has a light source for emitting vision fixation light, and the position of the light source and the emission direction of the vision fixation light can be arbitrarily adjusted. The external fixation lamp 15 is used for external vision fixation. The external vision fixation is a vision fixation method for causing the subject eye E (see FIG. 3) to make a circumnutation in an arbitrary direction or make a greater circumnutation than that under internal vision fixation by adjusting the position of the light source of the external fixation lamp 15, or adjusting the orientation of the subject eye E by guiding the visual line of the subject eye E or a fellow eye when the internal vision fixation cannot be performed.

The pedestal 13 is provided so as to be movable in the X direction and the Z direction (front-and-back and right-and-left directions) with respect to the base 11. An operating unit 16 is provided on the pedestal 13. Further, the measuring head 14 is provided on the pedestal 13 so as to be movable in the Y direction.

Further, the pedestal 13 is provided with an electric drive mechanism 17. The electric drive mechanism 17 is a publicly known actuator such as a motor drive mechanism, and under the control of an arithmetic control unit 22 (see FIG. 3) described later, the electric drive mechanism 17 causes the pedestal 13 to move in the X and Z directions, and causes the measuring head 14 to move in the Y direction. As a result, the measuring head 14 can move relatively to the subject eye E in the X, Y and Z directions.

The operating unit 16 is mounted on the pedestal 13 and at a position on the rear side (operator side) of the measuring head 14 in the Z direction. The operating unit 16 is provided with a manipulating lever 16a in addition to operating buttons for performing various operations (switching, etc. in the imaging mode) of the ophthalmologic apparatus 10.

The manipulating lever 16a is an operating member for manually moving the measuring head 14 in each of the X, Y, and Z directions. For example, in a case where the manipulating lever 16a is tilted in the Z direction (front-and-back direction) or the X direction (right-and-left direction), the measuring head 14 is moved in the Z direction or the X direction by the electric drive mechanism 17. Further, in a case where the manipulating lever 16a is rotated around its longitudinal axis, the measuring head 14 is moved in the Y direction (up-and-down direction) by the electric drive mechanism 17 according to a direction of the rotating operation of the manipulating lever 16a.

A fundus camera unit 14a and an OCT unit 14b shown in FIG. 3 described later are incorporated in the measuring head 14. A monitor 18 is provided on the back surface of the measuring head 14 on the rear side (operator side) in the Z direction. Further, a lens accommodating part 19 is provided on the front surface of the measuring head 14 on the front side (subject side) in the Z direction.

For example, a touch panel type liquid crystal display device is used as the monitor 18. The monitor 18 displays a screen for various imaging data of the subject eye E (see FIG. 3), an input screen for various setting operations, and the like. Note that the monitor 18 functions as the above-mentioned operating unit 16 when the input screen is displayed.

The lens accommodating part 19 accommodates an objective lens 43 that constitutes a part of the fundus camera unit 14a (see FIG. 3) and has an optical axis OA (see FIG. 3) parallel to the Z direction.

Further, although not shown, the lens accommodating part 19 is provided with a plurality of vision fixation holes (also referred to as fixation lamps) which are arranged at equal intervals along the circumferential direction of the objective lens 43 so as to surround the objective lens 43. Each vision fixation hole is used for peripheral vision fixation, imaging of a corner angle (the margin of an iris Er in FIG. 5) of the subject eye E (see FIG. 3), etc., and selectively emits vision fixation light in the Z direction according to an operation in the operating unit 16. Note that the peripheral vision fixation is a vision fixation method for causing each vision fixation hole to light selectively so that the subject eye E makes a great circumnutation in a desired direction.

Further, a stereo camera 20 is provided on the front surface of the measuring head 14 and in the vicinity of the lens accommodating part 19. The stereo camera 20 has a first camera 20a and a second camera 20b. The first camera 20a and the second camera 20b are arranged so as to sandwich the objective lens 43 from the left and right sides of the objective lens 43. The first camera 20a and the second camera 20b will be described later.

[Measuring Head]

Figure 3:
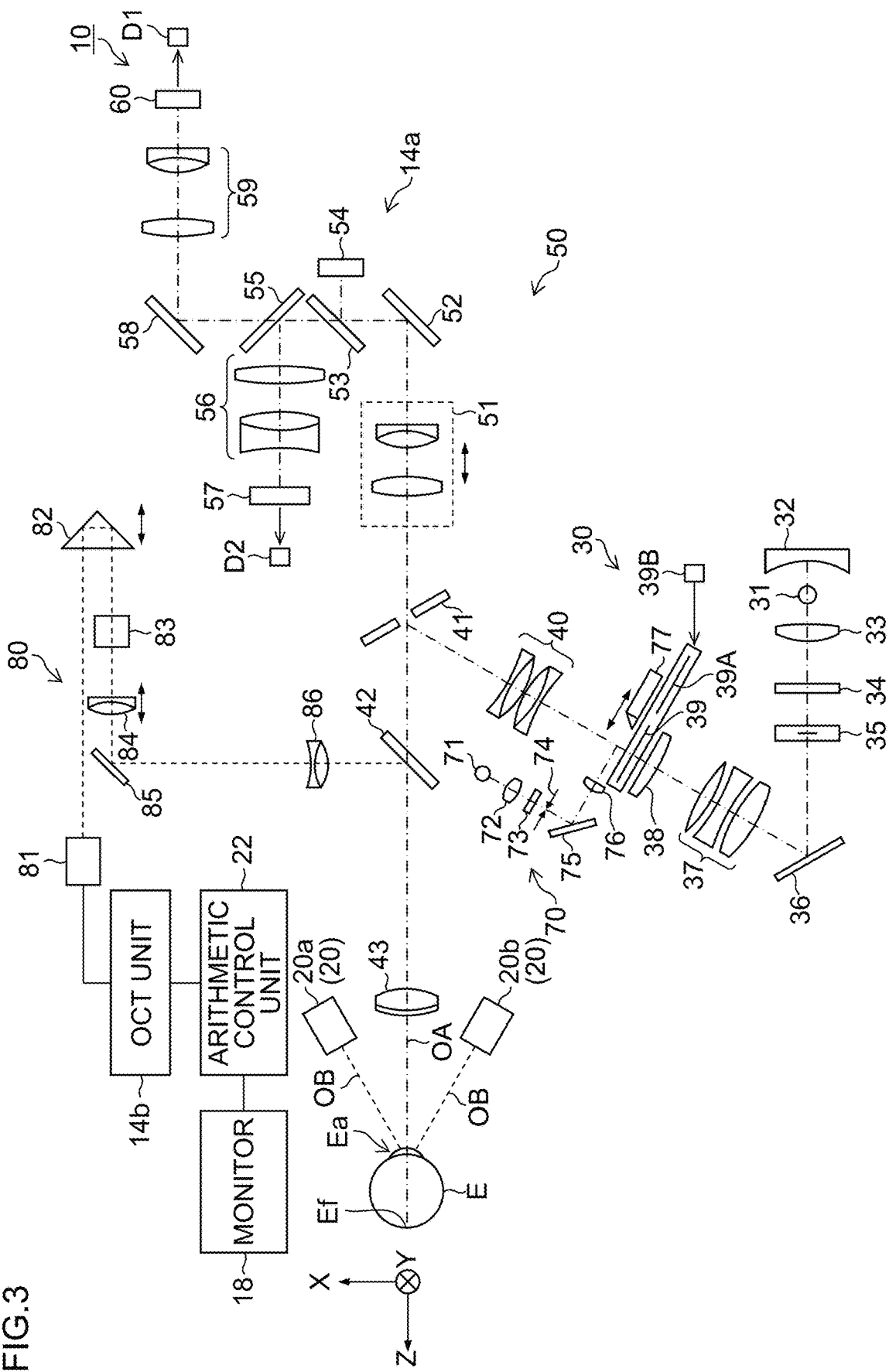
FIG. 3 is a schematic diagram showing an example of the configuration of a measuring head of the ophthalmologic apparatus.

FIG. 3 is a schematic diagram showing an example of the configuration of the measuring head 14 of the ophthalmologic apparatus 10. As shown in FIG. 3, the measuring head 14 includes the fundus camera unit 14a, the OCT unit 14b, and the stereo camera 20, and is connected to the arithmetic control unit 22.

The fundus camera unit 14a corresponds to the camera main body of the present invention, and has an optical system which is substantially similar to that of a conventional fundus camera. The fundus camera unit 14a irradiates the fundus Ef of the subject eye E with imaging illumination light (flash light or the like) through the objective lens 43, takes an image of the fundus Ef irradiated with the imaging illumination light, and outputs a fundus image D1. Further, the fundus camera unit 14a takes an image of an anterior ocular segment Ea of the subject eye E through the objective lens 43, and outputs an anterior ocular segment image D2 which is an observation image of the anterior ocular segment Ea.

The OCT unit 14b acquires an OCT image of the fundus Ef through the objective lens 43 and a part of the optical system of the fundus camera unit 14a.

The arithmetic control unit 22 is, for example, an arithmetic processing device such as a computer that is accommodated in the base 11 or the measuring head 14 and executes various arithmetic processing, control processing, etc.

<Fundus Camera Unit>

The fundus camera unit 14a includes an illumination optical system 30 and an imaging optical system 50, as an optical system for acquiring a fundus image D1 and an anterior ocular segment image D2.

The illumination optical system 30 irradiates the fundus Ef with illumination light (observation illumination light and imaging illumination light). The imaging optical system 50 directs fundus reflection light which is the illumination light reflected from the fundus Ef to, for example, CMOS (Complementary Metal Oxide Semiconductor) type or CCD (Charge Coupled Device) type imaging elements 57, 60 to take an image. Further, the imaging optical system 50 directs signal light output from an OCT optical system 80 (OCT unit 14b) to the fundus Ef, and also directs the signal light passing through the fundus Ef to the OCT optical system 80.

The illumination optical system 30 includes an observation light source 31, a reflection mirror 32, a condenser lens 33, a visible light cut filter 34, an imaging light source 35, a mirror 36, relay lenses 37, 38, a diaphragm 39, a small pupil diaphragm (small pupil diaphragm) 39A, a diaphragm switching mechanism 39B, a relay lens 40, a perforated mirror 41, a dichroic mirror 42, the objective lens 43, and the like.

In addition to the objective lens 43, the dichroic mirror 42, and the perforated mirror 41 described above, the imaging optical system 50 includes a focusing lens 51, a mirror 52, a half mirror 53, a visual target display unit 54, a dichroic mirror 55, a condenser lens 56, an imaging element 57, a mirror 58, a condenser lens 59, an imaging element 60, and the like.

For example, a halogen lamp, an LED (light emitting diode) or the like is used as the observation light source 31. The observation light source 31 emits observation illumination light. The observation illumination light emitted from the observation light source 31 is reflected by the reflection mirror 32 and passes through the visible light cut filter 34 via the condenser lens 33, to become near-infrared light. The observation illumination light having passed through the visible light cut filter 34 is once focused in the vicinity of the imaging light source 35, is reflected by the mirror 36, and passes through the relay lenses 37, 38, the diaphragm 39 (or the small pupil diaphragm 39A) and the relay lens 40. Then, the observation illumination light is reflected by a peripheral part of the perforated mirror 41 (a region around the perforated part), then passes through the dichroic mirror 42, and further refracted by the objective lens 43 to illuminate the fundus Ef.

The fundus reflection light of the observation illumination light is refracted by the objective lens 43, passes through the dichroic mirror 42, the perforated part formed in the central region of the perforated mirror 41, and the focusing lens 51, and then is reflected by the mirror 52. Further, the fundus reflection light passes through the half mirror 53 and then is reflected by the dichroic mirror 55 so that an image of the fundus reflection light is formed on a light receiving surface of the imaging element 57 by the condenser lens 56. The imaging element 57 captures (receives) the fundus reflection light and outputs an observation image of the fundus Ef to the arithmetic control unit 22 described later. The arithmetic control unit 22 causes the monitor 18 to display the observation image of the fundus Ef.

When the focus of the imaging optical system 50 is adjusted to the anterior ocular segment Ea of the subject eye E, the imaging element 57 captures an image of anterior ocular segment reflection light (cornea reflection light), and outputs an anterior ocular segment image D2 to the arithmetic control unit 22. In this case, the arithmetic control unit 22 causes the monitor 18 to display the anterior ocular segment image D2.

For example, a xenon lamp, an LED light source or the like is used as the imaging light source 35. The imaging light source 35 emits imaging illumination light (flash light) containing at least light in the visible wavelength band. The imaging illumination light emitted from the imaging light source 35 travels a path similar to the path for the observation illumination light described above, and irradiates the fundus Ef. The fundus reflection light of the imaging illumination light travels a path similar to the path for the fundus reflection light of the observation illumination light, is directed to the dichroic mirror 55, passes through the dichroic mirror 55, and then is reflected by the mirror 58, so that an image of the fundus reflection light is formed on a light receiving surface of the imaging element 60 by the condenser lens 59.

The imaging element 60 captures (receives) an image of the fundus reflection light, and outputs a fundus image D1 to the arithmetic control unit 22. The arithmetic control unit 22 causes the monitor 18 to display the fundus image D1 based on the imaging signal output from the imaging element 60. Note that the monitor 18 for displaying various observation images and the monitor 18 for displaying the fundus image D1 may be the same monitor or separate monitors.

The small pupil diaphragm 39A is adaptable to a small pupil eye whose pupil diameter d (see FIG. 5) is smaller than a standard pupil diameter (for example, 3 to 4 mm) to be a small pupil diameter (for example, less than 2 mm). The small pupil diaphragm 39A is held on the optical path of each illumination light by the diaphragm switching mechanism 39B so as to be freely insertable into and extractable from the optical path. The small pupil diaphragm 39A is formed to have an aperture diameter smaller than that of the standard diaphragm 39. The definitions of the small pupil diameter and the small pupil eye, and the specific shape and function of the small pupil diaphragm 39A are known in publicly known techniques, description on these matters is omitted here (see Japanese Patent Application Laid-Open No. H5-199997, and Japanese Patent Application Laid-Open No. 2013-165819). By inserting the small pupil diaphragm 39A onto the optical path of each illumination light, the fundus Ef can be illuminated with each illumination light even in a case where the subject eye E is a small pupil eye.

The diaphragm switching mechanism 39B is a publicly known actuator such as a motor drive mechanism that selectively inserts (arranges) the diaphragm 39 and the small pupil diaphragm 39A onto the optical path of the illumination light under the control of the arithmetic control unit 22. In the first embodiment, the arithmetic control unit 22 is adapted to drive the diaphragm switching mechanism 39B according to the switching operation input to the operating unit 16 so that the diaphragm 39 and the small pupil diaphragm 39A can be selectively arranged on the optical path of the illumination light. Note that the small pupil diaphragm 39A and the diaphragm switching mechanism 39B may be omitted in the first embodiment.

The visual target display unit 54 is used for internal vision fixation for projecting vision fixation light of a vision fixation target (bright spot image) onto the subject eye E through the objective lens 43. For example, a dot matrix liquid crystal display (LCD: Liquid Crystal Display), a matrix light emitting diode (LED), or the like is used as the visual target display unit 54. The visual target display unit 54 displays the vision fixation target. In addition, the visual target display unit 54 can arbitrarily set a display mode (shape, etc.) and a display position of the vision fixation target.

After a part of the vision fixation light of the vision fixation target displayed on the visual target display unit 54 is reflected by the half mirror 53, the part of the vision fixation light passes through the mirror 52, the focusing lens 51, the dichroic mirror 55, the perforated part of the perforated mirror 41, the dichroic mirror 42 and the objective lens 43, and then is projected onto the subject eye E. As a result, the vision fixation target, a visual target for visual acuity measurement, and the like are presented to the subject eye E through the objective lens 43.

The fundus camera unit 14a includes a focus optical system 70. The focus optical system 70 generates a split index for focusing on the fundus Ef. In addition to the objective lens 43, the dichroic mirror 42, and the perforated mirror 41 described above, the focus optical system 70 includes an LED 71, a relay lens 72, a split index plate 73, a two-hole diaphragm 74, a mirror 75, and a condenser lens 76, and a reflective rod 77.

The reflective surface of the reflective rod 77 is set on the optical path of the illumination optical system 30 in a case where focus adjustment is performed by the focus optical system 70. The focus light emitted from the LED 71 passes through the relay lens 72 and is split into two light beams by the split index plate 73. Then, the focus light passes through the two-hole diaphragm 74, the mirror 75 and the condenser lens 76, and temporarily forms an image on the reflective surface of the reflective rod 77, and then is reflected on the reflective surface to the relay lens 40. Further, the focus light passes through the relay lens 40, the perforated mirror 41, the dichroic mirror 42 and the objective lens 43, and then is projected onto the subject eye E.

The fundus reflection light of the focus light travels via the objective lens 43, the dichroic mirror 42 and the perforated part of the perforated mirror 41. After that, a part of the fundus reflection light passes through the dichroic mirror 55, travels via the focusing lens 51, the mirror 52, the half mirror 53, the dichroic mirror 55 and the condenser lens 56, and is imaged (image-captured) by the imaging element 57. The imaging element 57 captures an image of the fundus reflection light of the focus light, and outputs an imaging signal. As a result, the split index is displayed on the monitor 18 together with the observation image of the fundus Ef. The arithmetic control unit 22 analyzes the position of the split index and moves the focusing lens 51, etc. to automatically perform focusing as in the case of the prior art. Further, an operator may manually perform focusing based on the split index displayed on the monitor 18.

The dichroic mirror 42 branches the optical path of the OCT optical system 80 from the optical path for fundus imaging. The dichroic mirror 42 reflects light in a wavelength band used for OCT measurement, and transmits therethrough light for fundus imaging. A collimator lens unit 81, an optical path length changing unit 82, a Galvano scanner 83, a focusing lens 84, a mirror 85, and a relay lens 86 are provided in this order from the OCT unit 14b side, on the optical path of the OCT optical system 80.

The optical path length changing unit 82 includes, for example, a corner cube and a mechanism for moving the corner cube. The optical path length changing unit 82 is movable in a direction of an arrow shown in FIG. 3, and changes the optical path length of the OCT optical system 80. The change of the optical path length is used for correction of the optical path length according to the eye axial length of the subject eye E, adjustment of an interference state, and the like.

The Galvano scanner 83 changes the traveling direction of signal light passing through the optical path of the OCT optical system 80 so that the fundus Ef can be scanned with the signal light. The Galvano scanner 83 includes, for example, a Galvano mirror for scanning signal light in the X direction, a Galvano mirror for scanning signal light in the Y direction, and a mechanism for driving these Galvano mirrors independently of each other. As a result, the signal light can be scanned in any direction on an XY plane.

<OCT Unit>

The OCT unit 14b includes an interference optical system to be used for acquiring an OCT image of the fundus Ef. Like a publicly known OCT device, the OCT unit 14b divides low coherence light into reference light and signal light, causes the signal light traveling via the fundus Ef and the reference light traveling via the reference optical path to interfere with each other so as to generate interference light, and detects spectral components of the interference light. A detection result (detection signal) by the OCT unit 14b is output to the arithmetic control unit 22. Since the specific configuration of the OCT unit 14b is a publicly known technique (see, for example, Japanese Patent Application Laid-Open No. 2019-171221), specific description thereof is omitted here.

<Stereo Camera>

The first camera 20a and the second camera 20b constituting the stereo camera 20, and simultaneously (including substantially simultaneously) and sequentially take images (video images) of the anterior ocular segment Ea from different sides, that is, from the right and left sides in the present embodiment, and then output the anterior ocular segment image D2 to the arithmetic control unit 22. Reference character OB in FIG. 3 designates imaging optical axes of the first camera 20a and the second camera 20b.

[Arithmetic Control Unit]

Figure 4:
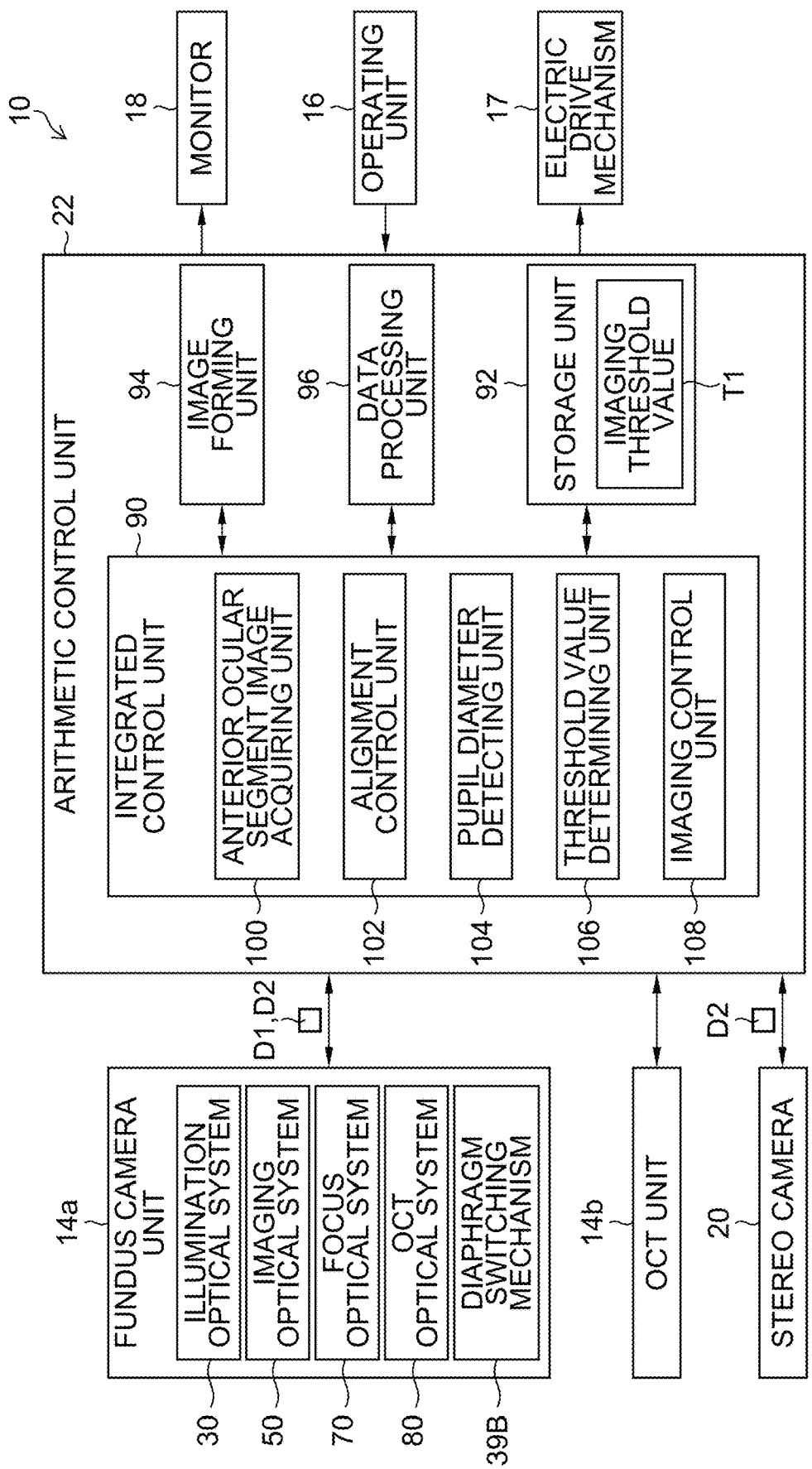
FIG. 4 is a functional block diagram of an arithmetic control unit of the ophthalmologic apparatus according to the first embodiment.

FIG. 4 is a functional block diagram of the arithmetic control unit 22 of the ophthalmologic apparatus 10 according to the first embodiment. As shown in FIG. 4, the arithmetic control unit 22 includes an integrated control unit 90, a storage unit 92, an image forming unit 94, a data processing unit 96, and the like. Further, the fundus camera unit 14a, the OCT unit 14b, the operating unit 16, the electric drive mechanism 17, the monitor 18, the stereo camera 20, and the like described above are connected to the arithmetic control unit 22.

The storage unit 92 stores image data of the fundus image D1, image data of the OCT image and the like in addition to control programs to be executed by the integrated control unit 90. Further, the storage unit 92 stores an imaging threshold value T1 determined by a threshold value determining unit 106 described later. Note that the storage unit 92 is not necessarily built in the ophthalmologic apparatus 10, but may be built in an external server (database).

The image forming unit 94 is used together with the OCT unit 14b to acquire an OCT image of the fundus Ef of the subject eye E, and analyzes a detection signal input from the OCT unit 14b to form an OCT image of the fundus Ef. A specific method for forming the OCT image is similar to that of a conventional OCT apparatus, and thus description thereof is omitted here. The data processing unit 96 performs image processing, etc. on the OCT image formed by the image forming unit 94 and the fundus image D1, etc. acquired by the fundus camera unit 14a.

The integrated control unit 90 performs integrated control on the operations of the respective components of the ophthalmologic apparatus 10. Further, before the fundus is imaged by the fundus camera unit 14a, the integrated control unit 90 determines based on the anterior ocular segment image D2 whether miosis is caused in the pupil Ep (see FIG. 5) of the subject eye E. Then, in a case where it is determined that miosis has been caused in the pupil Ep, the integrated control unit 90 suspends execution of the fundus imaging on the subject eye E until the miosis is settled (released). In a case where it is determined that the miosis in the pupil Ep has been settled, the integrated control unit 90 performs imaging control of executing the fundus imaging on the subject eye E. Note that in the first embodiment, the fundus imaging is performed on the subject eye E which is not a small pupil eye, but a normal eye having a standard pupil diameter described above. Therefore, the imaging control is performed during a second or subsequent fundus imaging operation in the sequential imaging mode or the right-and-left eye imaging mode.

The function of the integrated control unit 90 may be implemented by using various processors. The various processors include CPU (Central Processing Unit), GPU (Graphics Processing Unit), ASIC (Application Specific Integrated Circuit), and programmable logic device [for example, SPLD (Simple Programmable Logic Devices), CPLD (Complex Programmable Logic Device), FPGA (Field Programmable Gate Arrays)] and the like. The various functions of the integrated control unit 90 may be implemented by one processor, or may be implemented by a plurality of processors of the same type or different types.

The integrated control unit 90 functions as an anterior ocular segment image acquiring unit 100, an alignment control unit 102, a pupil diameter detecting unit 104, a threshold value determining unit 106, and an imaging control unit 108 during the fundus imaging on the subject eye E (in the sequential imaging mode, the right-and-left eye imaging mode). Note that what is referred to as "-unit" of the arithmetic control unit 22 may be "-circuit", "-device", or "-equipment". In other words, what is referred to as "-unit" may be formed from any of firmware, software, hardware, and a combination thereof. Further, only the functions related to the fundus imaging on the subject eye E in the integrated control unit 90 are shown in FIG. 4, and specific illustrations for the other functions are omitted because they are known in publicly known techniques.

The anterior ocular segment image acquiring unit 100 is connected in a wired manner or wirelessly to at least one of the fundus camera unit 14a (imaging element 57) and the stereo camera 20 via a communication interface (not shown), and acquires the anterior ocular segment image D2 from at least one of the fundus camera unit 14a and the stereo camera 20.

The anterior ocular segment image D2 is used for auto-alignment of the measuring head 14 with the subject eye E. The anterior ocular segment image D2 is also used to check the size of the pupil Ep (see FIG. 5) before the fundus imaging is performed on the subject eye E by the fundus camera unit 14a. Note that the present embodiment will be described on the assumption that the auto-alignment and the check of the size of the pupil Ep of the subject eye E before the fundus imaging are performed based on the anterior ocular segment image D2 captured by the stereo camera 20. When a measurement start operation is input by the operating unit 16, the anterior ocular segment image acquiring unit 100 repeatedly acquires the anterior ocular segment image D2 from the stereo camera 20 until the fundus imaging on the subject eye E is completed.

The alignment control unit 102 calculates the relative position (three-dimensional position) of the subject eye E to the measuring head 14 based on the anterior ocular segment image D2 acquired from the stereo camera 20 by the anterior ocular segment image acquiring unit 100 according to the measurement start operation (see Japanese Patent Application Laid-Open No. 2013-248376 described above). Next, the alignment control unit 102 drives the electric drive mechanism 17 based on a calculation result of the relative position of the subject eye E, and executes the auto-alignment of the measuring head 14 with respect to the subject eye E.

In a case where the imaging mode of the fundus imaging is the sequential imaging mode or the right-and-left eye imaging mode, the pupil diameter detecting unit 104 operates at least before the first fundus imaging operation on the subject eye E by the fundus camera unit 14a, and before the second and subsequent fundus imaging operations.

Here, "before the first fundus imaging operation" means "within a period of time until the first fundus imaging operation on the subject eye E is started" regardless of the type of the imaging mode. Further, "before the second and subsequent fundus imaging operations in the sequential imaging mode" means "a period of time from after the completion of the N-th fundus imaging operation until before the start of the (N+1)-th fundus imaging operation, when an arbitrary natural number is set to "N". Further, "before the second and subsequent fundus imaging operations in the right-and-left eye imaging mode" means "a period of time from after the completion of the fundus imaging on one of the right and left eyes until before the start of the fundus imaging on the other eye.

Figure 5:
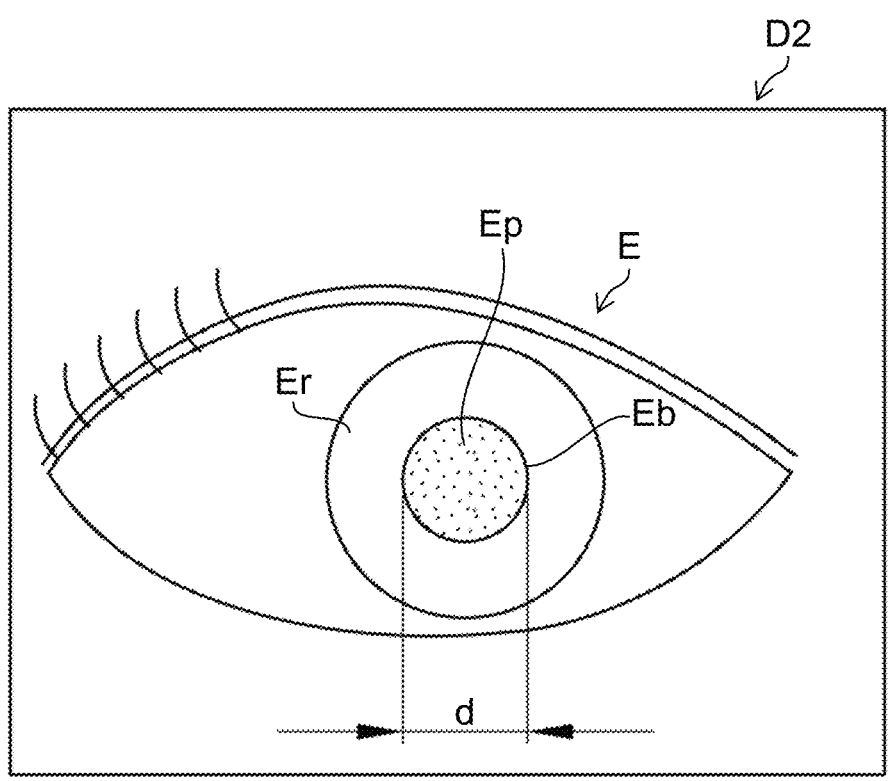
FIG. 5 is an explanatory diagram showing detection of a pupil diameter by a pupil diameter detecting unit.

FIG. 5 is an explanatory diagram showing the detection of the pupil diameter d by the pupil diameter detecting unit 104. As shown in FIG. 5 and FIG. 4 described above, the pupil diameter detecting unit 104 detects the pupil diameter d, which is the diameter of the pupil Ep of the subject eye E, based on the anterior ocular segment image D2 acquired from at least one of the first camera 20a and the second camera 20b of the stereo camera 20.

For example, the pupil diameter detecting unit 104 detects a pupillary margin Eb from the anterior ocular segment image D2 acquired from at least one of the first camera 20a and the second camera 20b. The pupillary margin Eb can be detected based on the difference in brightness between the pupil Ep and the iris Er in the anterior ocular segment image D2.

Next, the pupil diameter detecting unit 104 detects (calculates) the pupil diameter d by performing an elliptical approximation on the pupillary margin Eb and calculating the center coordinate of the pupillary margin Eb, based on the detection result of the pupillary margin Eb from the anterior ocular segment image D2. Since a method of detecting the pupil diameter d from the anterior ocular segment image D2 captured by the stereo camera 20 is a publicly known technique, specific description thereof will be omitted here (see, for example, Japanese Patent Application Laid-Open No. 2019-62982).

The pupil diameter detecting unit 104 executes the detection of the pupil diameter d at least once before the first fundus imaging operation on the subject eye E, and repeatedly executes the detection of the pupil diameter d at a plurality of times before the second and subsequent fundus imaging operations. As a result, at least before the second and subsequent fundus imaging operations on the subject eye E, the change in the pupil diameter d of the subject eye E can be detected in real time.

Based on the pupil diameter d detected by the pupil diameter detecting unit 104 before the first fundus imaging operation on the subject eye E, the threshold value determining unit 106 determines an imaging threshold value T1 (corresponding to a first threshold value of the present invention). The imaging threshold value T1 is a lower limit value of the pupil diameter d with which an excellent fundus image D1 can be acquired. The imaging threshold value T1 is a threshold value for determining whether the second and subsequent fundus imaging operations on the subject eye T should be executed. Here, since the subject eye E in the present embodiment is a normal eye, no miosis has been caused in the pupil Ep of the subject eye E before the first fundus imaging operation, that is, in a state where the subject eye E has not been irradiated with imaging illumination light (flash light) even once, and the pupil diameter d is also large enough to obtain an excellent fundus image D1. Therefore, the pupil diameter d of the subject eye E before the first fundus imaging operation can be used as a determination criterion (imaging threshold value T1) for determining whether miosis has been caused in the pupil Ep.

Specifically, the threshold value determining unit 106 determines the pupil diameter d detected by the pupil diameter detecting unit 104 before the first fundus imaging operation of the subject eye E, as the imaging threshold value T1 as it is. In a case where the pupil diameter detecting unit 104 detects pupil diameters d at a plurality of times, the threshold value determining unit 106 may determine a minimum value, an average value or the like of these detected pupil diameters d, as the imaging threshold value T1.

Further, in consideration of a detection error of the pupil diameter d detected by the pupil diameter detecting unit 104 and fluctuation of the pupil diameter d of the subject eye E, the threshold value determining unit 106 may determine, as the imaging threshold value T1, a value which is smaller by only a certain percentage than the pupil diameter d detected by the pupil diameter detecting unit 104 before the first fundus imaging operation on the subject eye E. The threshold value determining unit 106 determines the imaging threshold value T1 based on the pupil diameter d detected by the pupil diameter detecting unit 104 as described above. Therefore, even in a case where there are individual differences in the pupil diameter d for respective subjects, it is possible to individually determine imaging threshold values T1 corresponding to the respective subjects.

Returning to FIG. 4, the imaging control unit 108 controls the fundus camera unit 14a and the OCT unit 14b to control the imaging of the fundus image D1 and the OCT image of the fundus Ef of the subject eye E. In a case where the imaging mode of the fundus imaging is the normal mode, the imaging control unit 108 acquires the fundus image D1 by driving the fundus camera unit 14a to perform fundus imaging on the subject eye E after the auto alignment is completed. The control of the imaging of the fundus camera unit 14a by the imaging control unit 108 in the case where the imaging mode is the sequential imaging mode or the right-and-left eye imaging mode will be described later.

When performing OCT measurement on the fundus Ef, the imaging control unit 108 drives the OCT optical system 80, the OCT unit 14b, the image forming unit 94 and the like to acquire an OCT image of the fundus Ef after auto-alignment is completed.

Figure 6:
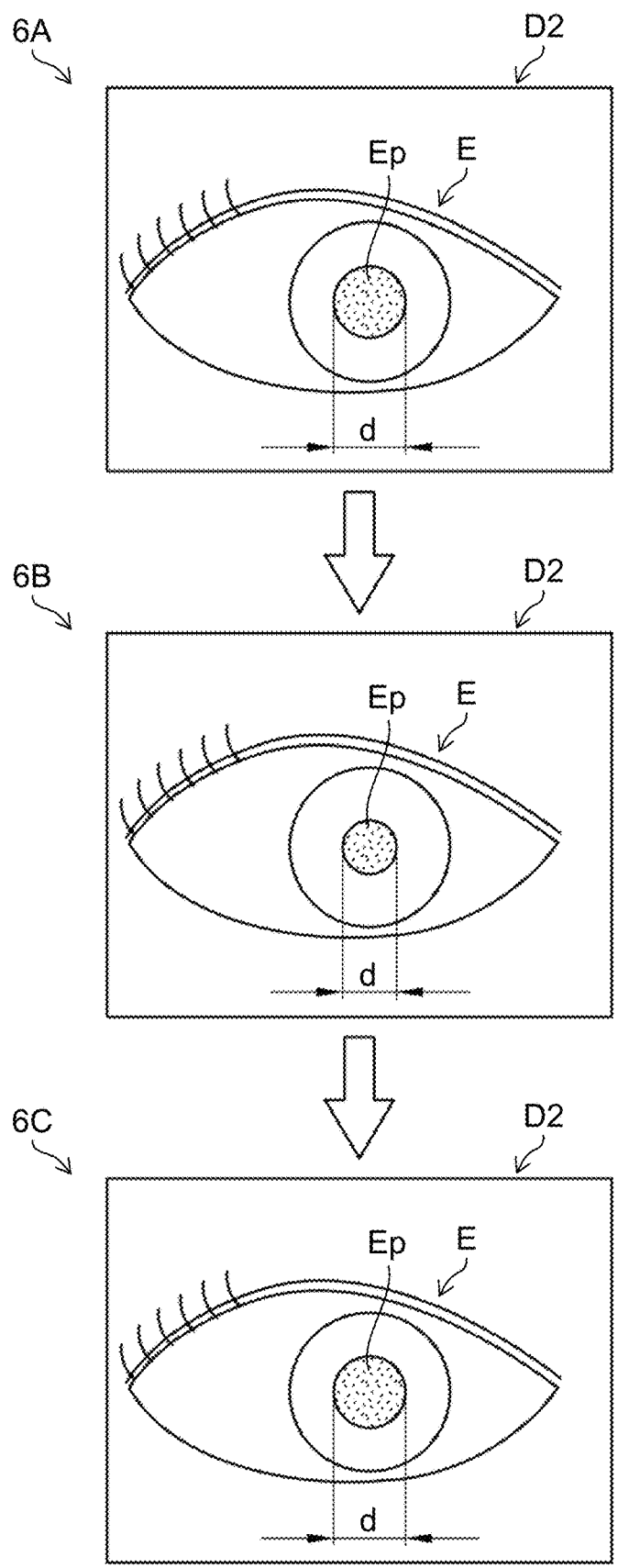
FIG. 6 is an explanatory diagram showing imaging control of a fundus camera unit in a sequential imaging mode by an imaging control unit.

FIG. 6 is an explanatory diagram showing the imaging control of the fundus camera unit 14a in the sequential imaging mode by the imaging control unit 108.

As designated by reference numeral 6A in FIG. 6, in a case where the sequential imaging mode is selected as the imaging mode, the imaging control unit 108 performs a first fundus imaging operation (first imaging of the present invention) on the subject eye E by the fundus camera unit 14a after the auto-alignment is completed. Since the subject eye E is a normal eye as described above, no miosis has been caused in the pupil Ep at the time of the first fundus imaging operation, and the fundus imaging can be performed in the same manner as in the case of the normal mode. When the first fundus imaging operation on the subject eye E is executed, miosis is caused in the pupil Ep due to irradiation of imaging illumination light (flash light).

As designated by reference numeral 6B in FIG. 6, prior to the second fundus imaging operation on the subject eye E, the imaging control unit 108 refers to the imaging threshold value T1 in the storage unit 92 based on the detection result of the pupil diameter d repeatedly detected by the pupil diameter detecting unit 104 and determines whether the pupil diameter d of the subject eye E reaches the imaging threshold value T1 or more. In a case where the pupil diameter d is less than the imaging threshold value T1, the imaging control unit 108 suspends execution of the second fundus imaging operation. In this case, the imaging control unit 108 waits until the pupil diameter d repeatedly detected by the pupil diameter detecting unit 104 reaches the imaging threshold value T1 or more.

As designated by reference numeral 6C in FIG. 6, in a case where the pupil diameter d of the subject eye E repeatedly detected by the pupil diameter detecting unit 104 reaches the imaging threshold value T1 or more, the imaging control unit 108 executes the second fundus imaging operation (second imaging of the present invention) on the subject eye E by the fundus camera unit 14*a*. As a result, the second fundus imaging operation on the subject eye E by the fundus camera unit 14*a* can be automatically executed in accordance with settlement of the miosis of the pupil Ep of the subject eye E.

Similarly, also in a third and subsequent fundus imaging operations on the subject eye E, the imaging control unit 108 likewise waits until the pupil diameter d of the subject eye E repeatedly detected by the pupil diameter detecting unit 104 reaches the imaging threshold value T1 or more, and when the pupil diameter d reaches the imaging threshold value T1 or more, the imaging control unit 108 executes the fundus imaging on the subject eye E by the fundus camera unit 14*a*.

Figure 7:
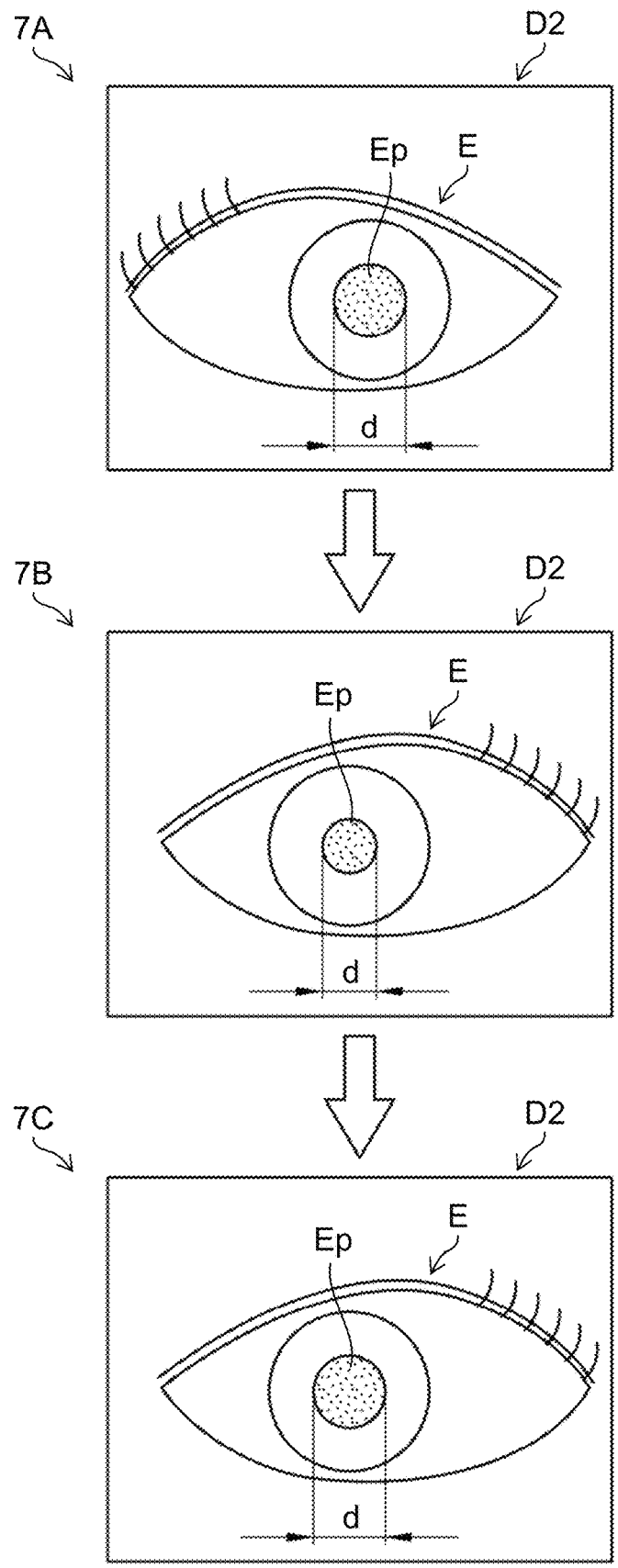
FIG. 7 is an explanatory diagram showing the imaging control of the fundus camera unit in a right-and-left eye imaging mode by the imaging control unit.

FIG. 7 is an explanatory diagram showing the imaging control of the fundus camera unit 14*a* in the right-and-left eye imaging mode by the imaging control unit 108.

As designated by reference numeral 7A in FIG. 7, in a case where the right-and-left eye imaging mode is selected as the imaging mode, the imaging control unit 108 performs the first fundus imaging operation on the subject eye E by the fundus camera unit 14*a*, that is, the fundus imaging operation on one (for example, the right eye) of the right and left eyes (corresponding to the first imaging of the present invention) after auto-alignment is completed. Since the subject eye E is a normal eye as described above, it is possible to perform the fundus imaging in the same manner as in the case of the first fundus imaging operation in the sequential imaging mode. When the fundus imaging on one of the right and left eyes is performed, miosis is caused in the pupil Ep of one of the right and left eyes due to irradiation of the imaging illumination light (flash light), and in conjunction with this miosis, miosis is also caused in the pupil Ep of the other eye (for example, the left eye) of the right and left eyes. Further, after the fundus imaging on one of the right and left eyes is completed, the auto-alignment of the measuring head 14 with the other eye of the right and left eyes is performed by the alignment control unit 102.

As designated by reference numeral 7B in FIG. 7, after the completion of auto-alignment and before the fundus imaging on the other eye of the right and left eyes, based on the detection result of the pupil diameter d repeatedly detected by the pupil diameter detecting unit 104, the imaging control unit 108 determines whether the pupil diameter d of the other eye of the right and left eyes reaches the imaging threshold value T1 or more as in the case of the second and subsequent fundus imaging operations in the sequential imaging mode. When the pupil diameter d of the other eye of the right and left eyes is less than the imaging threshold value T1, the imaging control unit 108 suspends execution of the fundus imaging on the other eye until the pupil diameter d reaches the imaging threshold value T1 or more.

As designated by reference numeral 7C in FIG. 7, in a case where the pupil diameter d repeatedly detected by the pupil diameter detecting unit 104 reaches the imaging threshold value T1 or more, the imaging control unit 108 performs the second fundus imaging operation on the subject eye E by the fundus camera unit 14*a*, that is, the fundus imaging on the other eye of the right and left eyes (corresponding to the second imaging of the present invention). As a result, the fundus imaging on the other eye by the fundus camera unit 14*a* can be automatically performed in accordance with settlement of the miosis of the other eye of the right and left eyes.

[Operation of Ophthalmologic Apparatus of First Embodiment]

Figure 8:
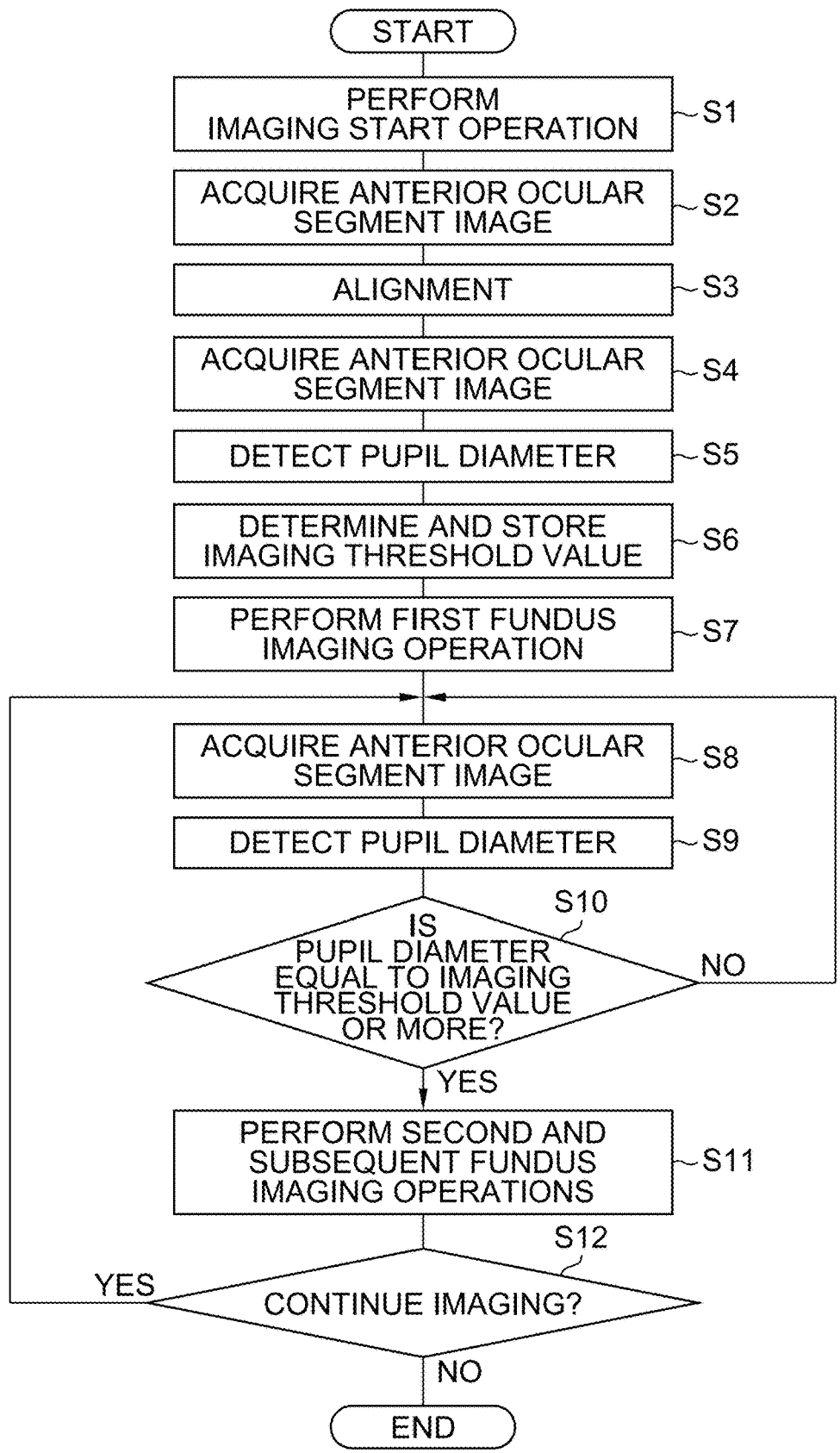
FIG. 8 is a flowchart showing the flow of fundus imaging processing for a subject eye by the ophthalmologic apparatus according to the first embodiment.

FIG. 8 corresponds to a control method of the fundus camera according to the present invention, and is a flowchart showing the flow of fundus imaging processing for the subject eye E by the ophthalmologic apparatus 10 according to the first embodiment. Here, description will be made by exemplifying a case where the sequential imaging mode or the right-and-left eye imaging mode is selected as the imaging mode of the fundus imaging.

When an operator inputs an imaging start operation on the operating unit 16 after the face of a subject is supported by the face supporting part 12 (step S1), the integrated control unit 90 functions as the anterior ocular segment image acquiring unit 100, the alignment control unit 102, the pupil diameter detecting unit 104, the threshold value determining unit 106, and the imaging control unit 108. The anterior ocular segment image acquiring unit 100 starts sequential imaging on the anterior ocular segment Ea of the subject eye E by the stereo camera 20. As a result, the anterior ocular segment image acquiring unit 100 repeatedly acquires the anterior ocular segment image D2 from the stereo camera 20 (step S2).

After the alignment control unit 102 detects the relative position of the subject eye E to the measuring head 14 based on the anterior ocular segment image D2 acquired from the stereo camera 20 by the anterior ocular segment image acquiring unit 100, the alignment control unit 102 drives the electric drive mechanism 17 to perform the auto-alignment of the measuring head 14 with the subject eye E (step S3).

Further, based on the anterior ocular segment image D2 acquired by the anterior ocular segment image acquiring unit 100 (step S4, corresponding to an anterior ocular segment image acquiring step of the present invention), the pupil diameter detecting unit 104 detects of the pupil diameter d of the subject eye E at least once or more (step S5, corresponding to a pupil diameter detecting step of the present invention). Then, the threshold value determining unit 106 determines the imaging threshold value T1 based on the detection result of the pupil diameter d by the pupil diameter detecting unit 104, and stores the imaging threshold value T1 into the storage unit 92 (step S6). Here, the timings of the steps S4 and S5 are not particularly limited as long as the steps S4 and S5 are performed before the first fundus imaging operation on the subject eye E by the fundus camera unit 14*a*, and the steps S4 and S5 may be executed before auto-alignment or during auto-alignment.

When the auto-alignment and the storage of the imaging threshold value T1 are completed, as designated by reference numeral 6A in FIG. 6 and reference numeral 7A in FIG. 7 described above, the imaging control unit 108 causes the fundus camera unit 14*a* to perform the first fundus imaging operation on the subject eye E (step S7). As a result, the fundus camera unit 14*a* performs irradiation of the fundus Ef of the subject eye E with imaging illumination light (flash light) and imaging on the fundus Ef, and outputs a fundus image D1 to the arithmetic control unit 22. At this time, the subject eye E is a normal eye, and thus no miosis has been caused before the first fundus imaging operation. Therefore, an excellent fundus image D1 is obtained.

When the first fundus imaging operation on the subject eye E is performed, as designated by reference numeral 6B in FIG. 6 and reference numeral 7B in FIG. 7 described above, miosis is caused in the pupil Ep of the subject eye E (both the eyes) due to the irradiation of the imaging illumination light from the fundus camera unit 14*a*.

In a case where the imaging mode of the fundus imaging is the sequential imaging mode, after the first fundus imaging operation on the subject eye E is completed, the acquisition of an anterior ocular segment image D2 from the stereo camera 20 by the anterior ocular segment image acquiring unit 100 (step S8, corresponding to an anterior ocular segment image acquiring step of the present invention) and the detection of the pupil diameter d by the pupil diameter detecting unit 104 (step S9, corresponding to a pupil diameter detecting step of the present invention) are subsequently performed. On the other hand, in a case where the imaging mode of the fundus imaging is the right-and-left eye imaging mode, although not shown, after the first fundus imaging operation on the subject eye E is completed, in parallel with the processing of the steps S8 and S9, the alignment control unit 102 performs the auto-alignment of the measuring head 14 with the other eye of the right and left eyes.

Then, the imaging control unit 108 is held in a standby state until the pupil diameter d repeatedly detected by the pupil diameter detecting unit 104 reaches the imaging threshold value T1 or more, and repetitive control is performed so that the processing of the steps S8 and S9 is repeatedly executed. (NO in step S10).

Next, as designated by reference numeral 6C in FIG. 6 and reference numeral 7C in FIG. 7, the imaging control unit 108 causes the fundus camera unit 14a to perform the second fundus imaging operation on the subject eye E (the other eye of the right and left eyes) when the pupil diameter d repeatedly detected by the pupil diameter detecting unit 104 reaches the imaging threshold value T1 or more (YES in step S10, step S11). As a result, the fundus camera unit 14a performs the irradiation of the fundus Ef of the subject eye E with the imaging illumination light (flash light) and the imaging on the fundus Ef, and outputs a fundus image D1 to the arithmetic control unit 22. Since the second fundus imaging operation is automatically performed by the fundus camera unit 14a in accordance with the settlement of the miosis of the subject eye E, an excellent fundus image D1 can be obtained. Here, step S11 corresponds to an imaging control step of the present invention.

Hereinafter, when the third and subsequent fundus imaging operations (in the sequential imaging mode) on the subject eye E is performed, the processing from step S8 to step S11 are repeatedly executed (step S12).

Effect of First Embodiment

As described above, according to the first embodiment, in the second and subsequent fundus imaging operations in which miosis has been caused in the subject eye E, it is possible to suspend execution of fundus imaging until the pupil diameter d of the subject eye E reaches the imaging threshold value T1 or more based on the detection result of the pupil diameter detecting unit 104 and perform fundus imaging when the pupil diameter d reaches the imaging threshold value T1 or more. As a result, it is possible to reliably perform fundus imaging in a state where no miosis is caused in the pupil Ep of the subject eye E, so that an excellent fundus image D1 can be obtained.

Second Embodiment

Next, an ophthalmologic apparatus 10 according to a second embodiment of the present invention will be described. In the ophthalmologic apparatus 10 according to the first embodiment, when miosis is caused in the pupil Ep of the subject eye E due to irradiation of the imaging illumination light, execution of the fundus imaging is suspended until the pupil diameter d of the subject eye E reaches the imaging threshold value T1 or more. However, depending on the subject eye E (subject), it may take some time until the miosis of the pupil Ep is settled. Therefore, in the ophthalmologic apparatus 10 according to the second embodiment, when it takes some time until the miosis of the pupil Ep caused by the irradiation of the imaging illumination light is settled, the fundus imaging on the subject eye E is performed by using the small pupil diaphragm 39A.

The ophthalmologic apparatus 10 according to the second embodiment has basically the same configuration as the ophthalmologic apparatus 10 according to the first embodiment, except that the function of the imaging control unit 108 is partially different from that in the first embodiment. Components having the same functions or configurations as those of the first embodiment are designated by the same reference numerals or reference characters, and the description thereof will be omitted.

Figure 9:
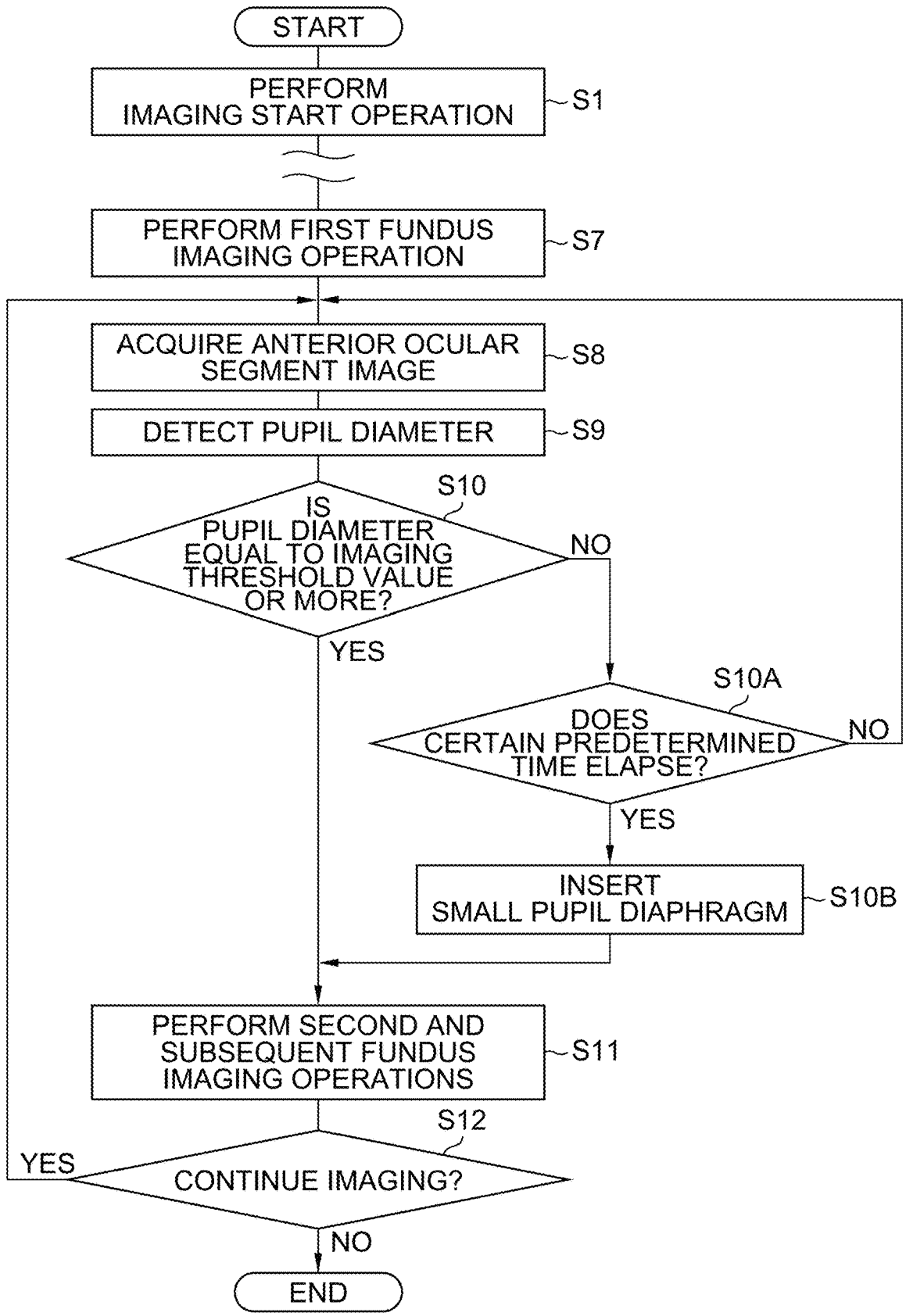
FIG. 9 is a flowchart showing the flow of fundus imaging processing for a subject eye by an ophthalmologic apparatus according to a second embodiment.

FIG. 9 is a flowchart showing the flow of fundus imaging processing for the subject eye E by the ophthalmologic apparatus 10 according to the second embodiment. The processing from step S1 to step S9 is the same as that of the first embodiment described with reference to FIG. 8, and thus specific description thereof will be omitted.

As shown in FIG. 9, the imaging control unit 108 according to the second embodiment suspends execution of the second fundus imaging operation on the subject eye E when the pupil diameter d repeatedly detected by the pupil diameter detecting unit 104 is less than the imaging threshold value T1 after the first fundus imaging operation on the subject eye E (NO in step S10). Then, the imaging control unit 108 starts to measure a standby time. When the pupil diameter d of the subject eye E reaches the imaging threshold value T1 or more based on the detection result of the pupil diameter detecting unit 104 within a certain predetermined time, the imaging control unit 108 executes the processing of the steps S11 and S12 in the same manner as in the case of the first embodiment (see FIG. 8) (NO in step S10A).

On the other hand, when the pupil diameter d is less than the imaging threshold value T1 based on the detection result of the pupil diameter detecting unit 104 even after a lapse of a certain predetermined time, the imaging control unit 108 drives the diaphragm switching mechanism 39B to insert the small pupil diaphragm 39A onto the optical path of the illumination light (YES in step S10A, step S10B). As a result, even in a state where the miosis of the pupil Ep of the subject eye E has not yet been settled, the fundus Ef can be illuminated with each illumination light (imaging illumination light, etc.) by using the small pupil diaphragm 39A adaptable to small pupil eyes.

Next, the imaging control unit 108 causes the fundus camera unit 14a to perform the second fundus imaging operation on the subject eye E (step S11). In this case, the imaging control unit 108 functions as a first special imaging control unit of the present invention. Since the small pupil diaphragm 39A makes it possible for the fundus camera unit 14a to image the fundus Ef being irradiated with the imaging illumination light, an excellent fundus image D1 can be obtained. When the fundus imaging is completed, the imaging control unit 108 drives the diaphragm switching mechanism 39B to retract the small pupil diaphragm 39A from the optical path of the illumination light, and inserts the diaphragm 39 into this optical path.

Hereinafter, when the third and subsequent fundus imaging operations (in the sequential imaging mode) on the subject eye E are performed, the above-mentioned series of processing is repeatedly executed (step S12).

As described above, in the second embodiment, when it takes time until the miosis of the pupil Ep of the subject eye E caused by the irradiation of the imaging illumination light has been settled, the fundus image D1 can be captured in a short time by performing the fundus imaging on the subject eye E in a state where the small pupil diaphragm 39A is inserted on the optical path of the illumination light.

In the second embodiment, in a case where it takes time until the miosis of the pupil Ep of the subject eye E has been settled, the small pupil diaphragm 39A is inserted (arranged) on the optical path of the illumination light. However, the small pupil diaphragm 39A in the second embodiment is not particularly limited as long as the diaphragm diameter thereof is smaller than at least that of the diaphragm 39, and a diaphragm having a diaphragm diameter larger than that of a general small pupil diaphragm 39A may be used. Further, it is possible to use a variable diaphragm (including a liquid crystal shutter) whose diaphragm diameter can be adjusted according to the amount of miosis of the pupil Ep of the subject eye E, as the small pupil diaphragm 39A according to the second embodiment.

Third Embodiment

Figure 10:
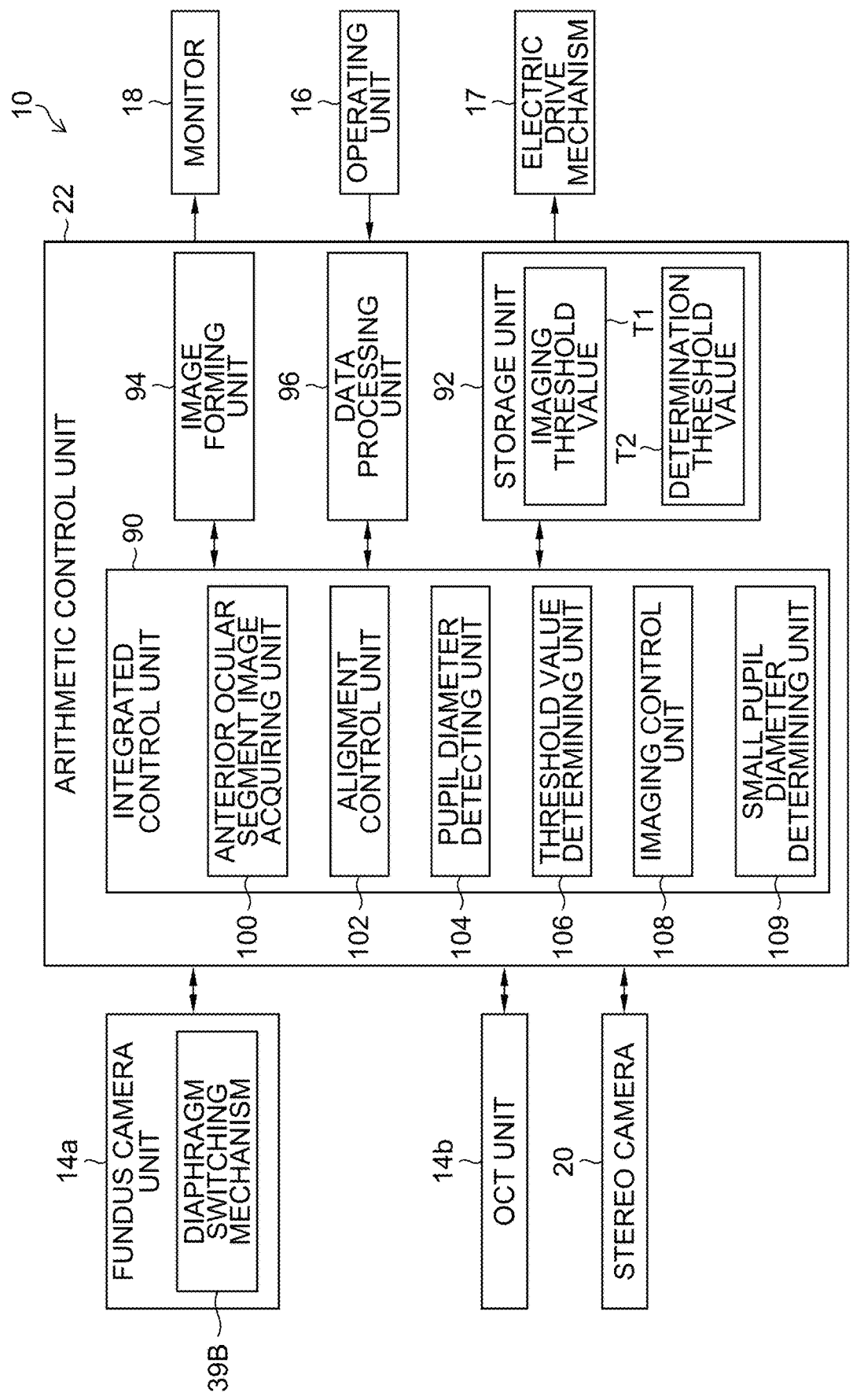
FIG. 10 is a functional block diagram of an arithmetic control unit of an ophthalmologic apparatus according to a third embodiment.

FIG. 10 is a functional block diagram of an arithmetic control unit 22 of an ophthalmologic apparatus 10 according to a third embodiment. The ophthalmologic apparatus 10 of each of the above-mentioned embodiments performs the fundus imaging on a normal eye as a subject eye E, but the ophthalmologic apparatus 10 according to the third embodiment performs the fundus imaging on a small pupil eye as a subject eye E. Specifically, in the ophthalmologic apparatus 10 according to the third embodiment, in a case where the fundus imaging is performed on a small pupil eye, the fundus imaging is performed on the subject eye E in a state where the small pupil diaphragm 39A is automatically inserted on the optical path of illumination light.

The ophthalmologic apparatus 10 according to the third embodiment has basically the same configuration as the ophthalmologic apparatus 10 of each of the above-mentioned embodiments except that the integrated control unit 90 functions as a small pupil diameter determining unit 109, the functions of the imaging control unit 108 are partially different, and a determination threshold value T2 is stored in the storage unit 92. Therefore, components having the same functions or configurations as those of each of the above-mentioned embodiments are designated by the same reference numerals or reference characters, and the description thereof will be omitted.

The small pupil diameter determining unit 109 determines whether the subject eye E is a small pupil eye before the first fundus imaging operation on the subject eye E. The determination threshold value T2 (corresponding to a second threshold value of the present invention) is a threshold value to be used for determination by the small pupil diameter determining unit 109, and the determination threshold value T2 is set to a value smaller than the imaging threshold value T1, for example, 2 mm (see Japanese Patent Application Laid-Open No. 2013-165819). Note that the determination threshold value T2 may be individually prepared for each of various conditions related to the pupil diameter d of the small pupil eye such as the age of a subject.

The imaging control unit 108 according to the third embodiment functions as a second special imaging control unit of the present invention in a case where the subject eye E is a small pupil eye, and performs the fundus imaging on the subject eye E by using the small pupil diaphragm 39A.

Figure 11:
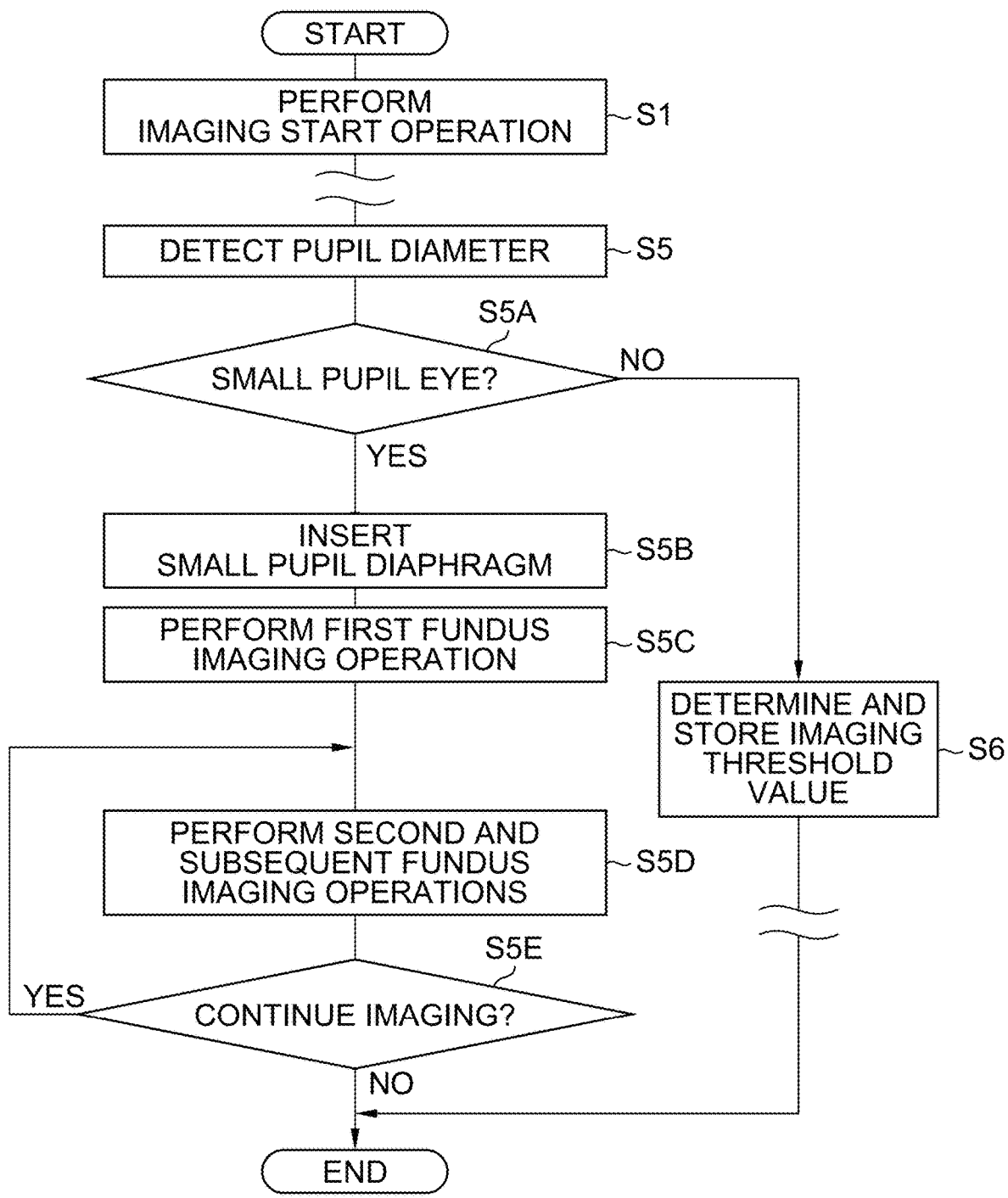
FIG. 11 is a flowchart showing the flow of fundus imaging processing for a subject eye by the ophthalmologic apparatus according to the third embodiment.

FIG. 11 is a flowchart showing the flow of fundus imaging processing on the subject eye E by the ophthalmologic apparatus 10 according to the third embodiment. Since the processing from step S1 to step S5 are the same as that of the first embodiment described with reference to FIG. 8 described above, specific description thereof will be omitted.

As shown in FIG. 11, before the first fundus imaging operation on the subject eye E, the small pupil diameter determining unit 109 refers to the determination threshold value T2 in the storage unit 92 based on the pupil diameter d detected by the pupil diameter detecting unit 104 to determine whether the subject eye E is a small pupil eye (step S5A). Specifically, the small pupil diameter determining unit 109 determines whether the subject eye E is a small pupil eye based on whether the pupil diameter d is less than the determination threshold value T2.

In a case where the subject eye E is determined to be a normal eye by the small pupil diameter determining unit 109, the same processing as that of each of the above-mentioned embodiments (see FIGS. 8 and 9) is executed (No in step S5A).

On the other hand, in a case where it is determined by the small pupil diameter determining unit 109 that the subject eye E is a small pupil eye, the imaging control unit 108 drives the diaphragm switching mechanism 39B to insert the small pupil diaphragm 39A onto the optical path of illumination light (YES in step S5A, step S5B). Then, the imaging control unit 108 causes the fundus camera unit 14a to perform the first fundus imaging operation on the subject eye E in a state where the small pupil diaphragm 39A is inserted on the optical path (step S5C). Because the fundus imaging is performed on the subject eye E with the small pupil diaphragm 39A adaptable to the small pupil eye, an excellent fundus image D1 can be obtained even when the subject eye E is a small pupil eye.

In a case where the imaging mode is the right-and-left eye imaging mode, although not shown, upon completion of the first fundus imaging operation on the subject eye E, the alignment control unit 102 performs auto-alignment of the measuring head 14 with the other eye of the right and left eyes.

Next, the imaging control unit 108 causes the fundus camera unit 14a to perform the second fundus imaging operation on the subject eye E in a state where the small pupil diaphragm 39A is inserted on the optical path of illumination light (step S5D). As a result, an excellent fundus image D1 can be obtained as in the case of the first fundus imaging operation.

Hereinafter, when the third and subsequent fundus imaging operations (in the sequential imaging mode) is performed on the subject eye E, the processing of step S5D is repeatedly executed (step S5E).

As described above, in the third embodiment, it is possible to determine based on the detection result of the pupil diameter detecting unit 104 whether the subject eye E is a small pupil eye, and in a case where it is determined that the subject eye E is a small pupil eye, it is also possible to automatically insert the small pupil diaphragm 39A onto the optical path of the illumination light and then perform the fundus imaging on the subject eye E by the fundus camera unit 14a. As a result, an excellent fundus image D1 can be obtained even in a case where the subject eye E is a small pupil eye. Further, the small pupil diaphragm 39A can be automatically inserted onto the optical path of the illumination light without the operator's switching operation on the operating unit 16.

Fourth Embodiment

Figure 12:
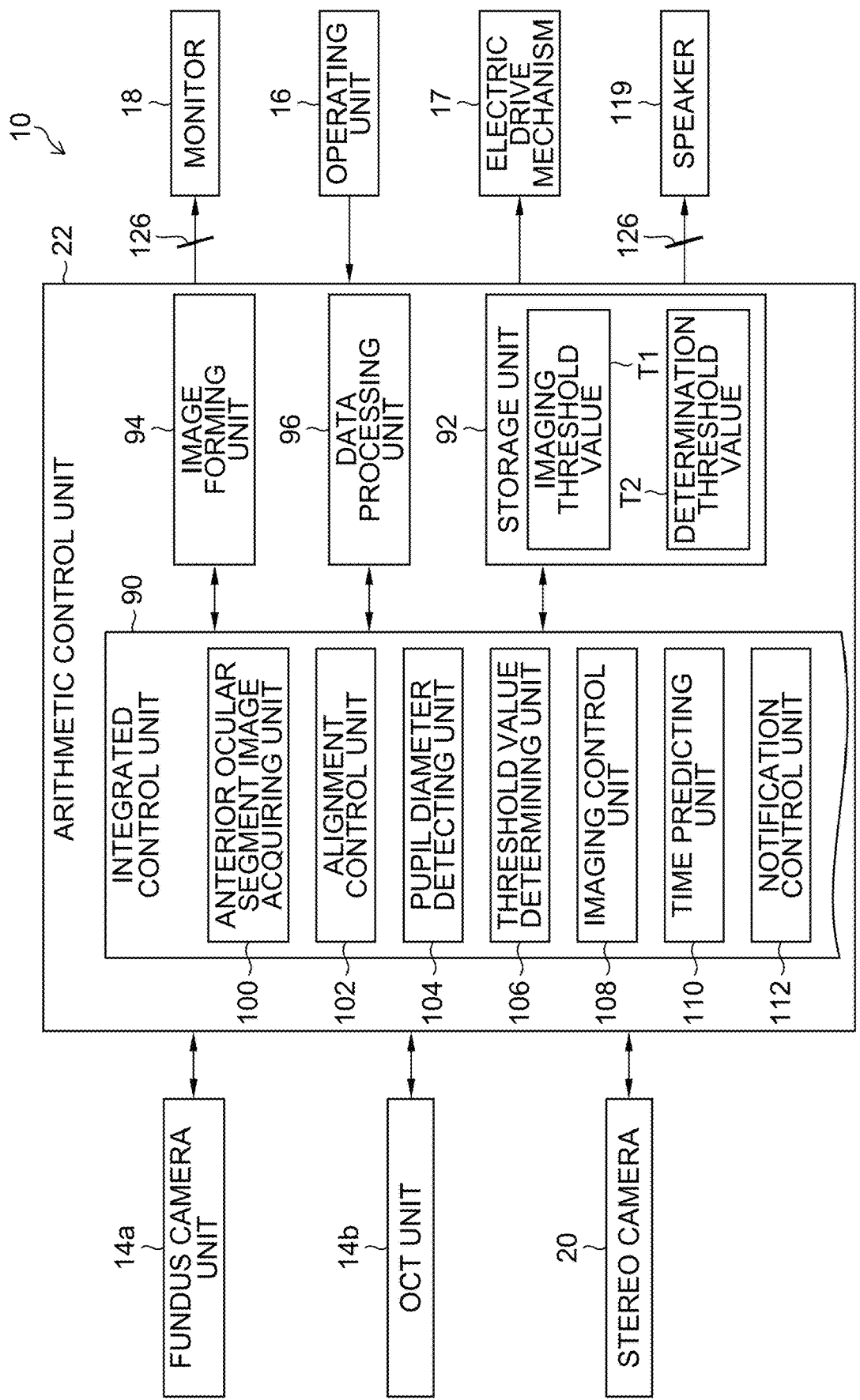
FIG. 12 is a functional block diagram of an arithmetic control unit of an ophthalmologic apparatus according to a fourth embodiment.

FIG. 12 is a functional block diagram of an arithmetic control unit 22 of an ophthalmologic apparatus 10 according to a fourth embodiment. The ophthalmologic apparatus 10 according to each of the above-mentioned embodiments suspends the execution of the fundus imaging until the pupil diameter d reaches the imaging threshold value T1 or more in the second and subsequent fundus imaging operations on the subject eye E (excluding the small pupil eye). In this case, it is unknown when the fundus imaging is to be performed. Therefore, the ophthalmologic apparatus 10 according to the fourth embodiment predicts a return time t required until the pupil diameter d of the subject eye E in which miosis has been caused due to irradiation of imaging illumination light increases up to the imaging threshold value T1, and notifies the predicted return time t.

Note that the ophthalmologic apparatus 10 according to the fourth embodiment has basically the same configuration as the ophthalmologic apparatus 10 according to each of the above-mentioned embodiments except that a speaker 119 is connected to the arithmetic control unit 22 and the integrated control unit 90 functions as a time predicting unit 110 and a notification control unit 112. Therefore, components having the same functions or configurations as those of each of the above-mentioned embodiments are designated by the same reference numerals or reference characters, and the description thereof will be omitted. Further, the fourth embodiment will be described on the assumption that the subject eye E is a normal eye.

Figure 13:
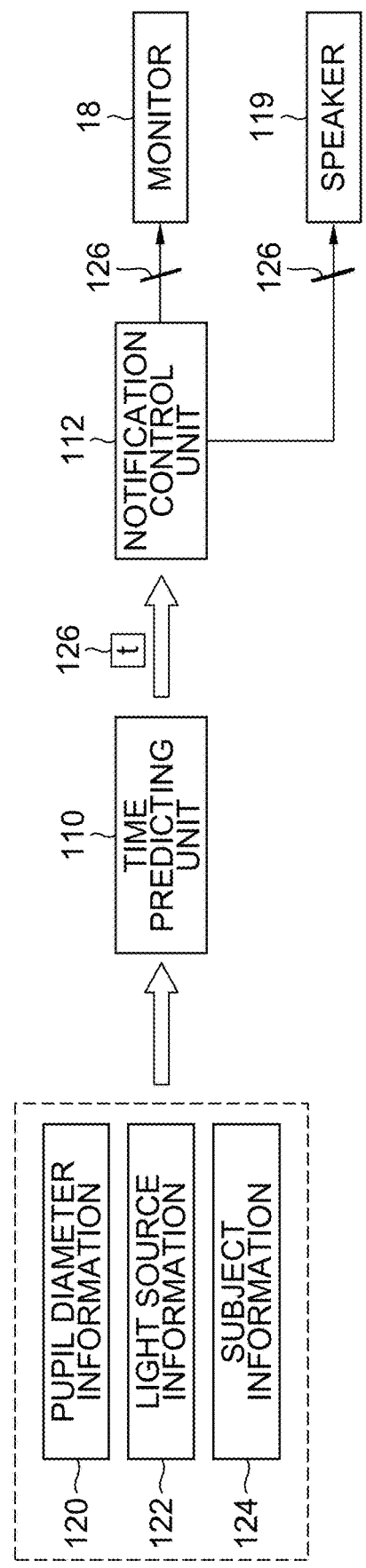
FIG. 13 is an explanatory diagram showing a first example of prediction of a return time by a time predicting unit.

FIG. 13 is an explanatory diagram showing a first example of prediction of the return time t by the time predicting unit 110. As shown in FIG. 13 and FIG. 12 described above, when the first fundus imaging operation is performed on the subject eye E, the time predicting unit 110 predicts the return time t based on pupil diameter information 120 indicating a detection result of a new pupil diameter d by the pupil diameter detecting unit 104, light source information 122 indicating a type of the imaging light source 35, and subject information 124 indicating age, disease and the like of the subject.

The return time t varies according to the amount of miosis of the pupil Ep (pupil diameter d) in the first fundus imaging operation on the subject eye E, and for example, the return time t becomes longer as the amount of miosis is larger. Further, the return time t varies according to the type of the imaging light source 35 (the type of the imaging illumination light), for example, the return time t becomes longer or conversely shorter depending on specific imaging light sources 35. Further, the return time t also varies according to the age, disease and the like of the subject. For example, when the subject is elderly or has a disease such as eye strain, the return time t becomes longer. Therefore, the time predicting unit 110 can predict the return time t based on the pupil diameter information 120, the light source information 122, and the subject information 124. Note that the light source information 122 is stored in the storage unit 92 in advance, and the subject information 124 can be input via the operating unit 16 or obtained from a hospital database or the like.

For example, the time predicting unit 110 predicts the return time t by referring to a data table generated in advance based on the pupil diameter information 120, the light source information 122, and the subject information 124. Further, the time predicting unit 110 may predict the return time t by using a trained model (learned model) into which the pupil diameter information 120, the light source information 122, and the subject information 124 are input and from which the return time t is output. The time predicting unit 110 outputs return time information 126 indicating an prediction result of the return time t to the notification control unit 112. The return time t (return time information 126) predicted by the time predicting unit 110 is updated every time the pupil diameter detecting unit 104 detects a new pupil diameter d, that is, every time the pupil diameter information 120 is updated.

The time predicting unit 110 according to the present embodiment predicts the return time t based on the pupil diameter information 120, the light source information 122, and the subject information 124. However, the light source information 122 and the subject information 124 are not indispensable, and the return time t may be predicted based on only the pupil diameter information 120. In other words, the time predicting unit 110 may predict the return time t based on at least the pupil diameter information 120.

Figure 14:
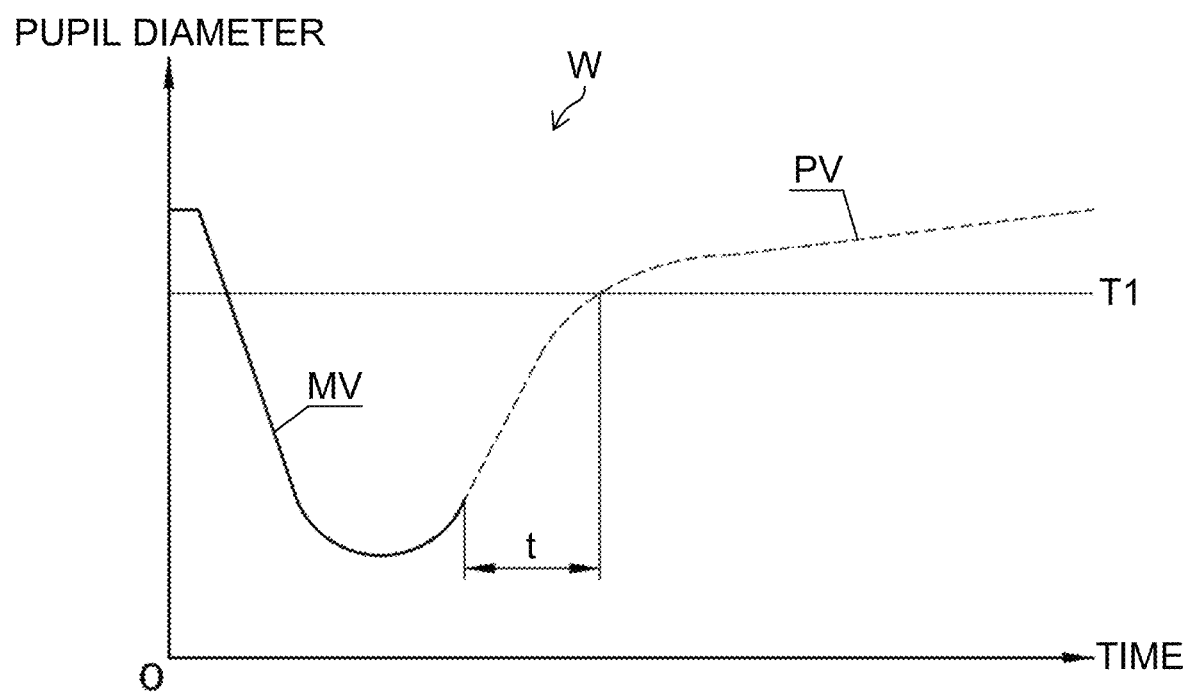
FIG. 14 is an explanatory diagram showing a second example of the prediction of the return time by the time predicting unit.

FIG. 14 is an explanatory diagram showing a second example of the prediction of the return time t by the time predicting unit 110. As shown in FIG. 14, a change of the pupil diameter d over time, from the time when miosis is caused in the pupil Ep of the subject eye E due to irradiation of imaging illumination light until the time when the miosis of the pupil Ep is settled to restore an original state is generally represented by a waveform W as illustrated in FIG. 14. Therefore, the time predicting unit 110 can calculate prediction values PV (indicated by a dotted line in FIG. 14) of the change of the pupil diameter d over time, by calculating the waveform W based on a change (indicated by a solid line in FIG. 14) of actual measurement values MV of the pupil diameter d over time, which are repeatedly obtained by the pupil diameter detecting unit 104 after the first imaging operation on the subject eye E according to a method such as a publicly-known fitting method. As a result, the time predicting unit 110 can predict the return time t and output the return time information 126 to the notification control unit 112 before the miosis of the pupil Ep of the subject eye E is settled (before the pupil diameter d reaches the imaging threshold value T1).

Figure 15:
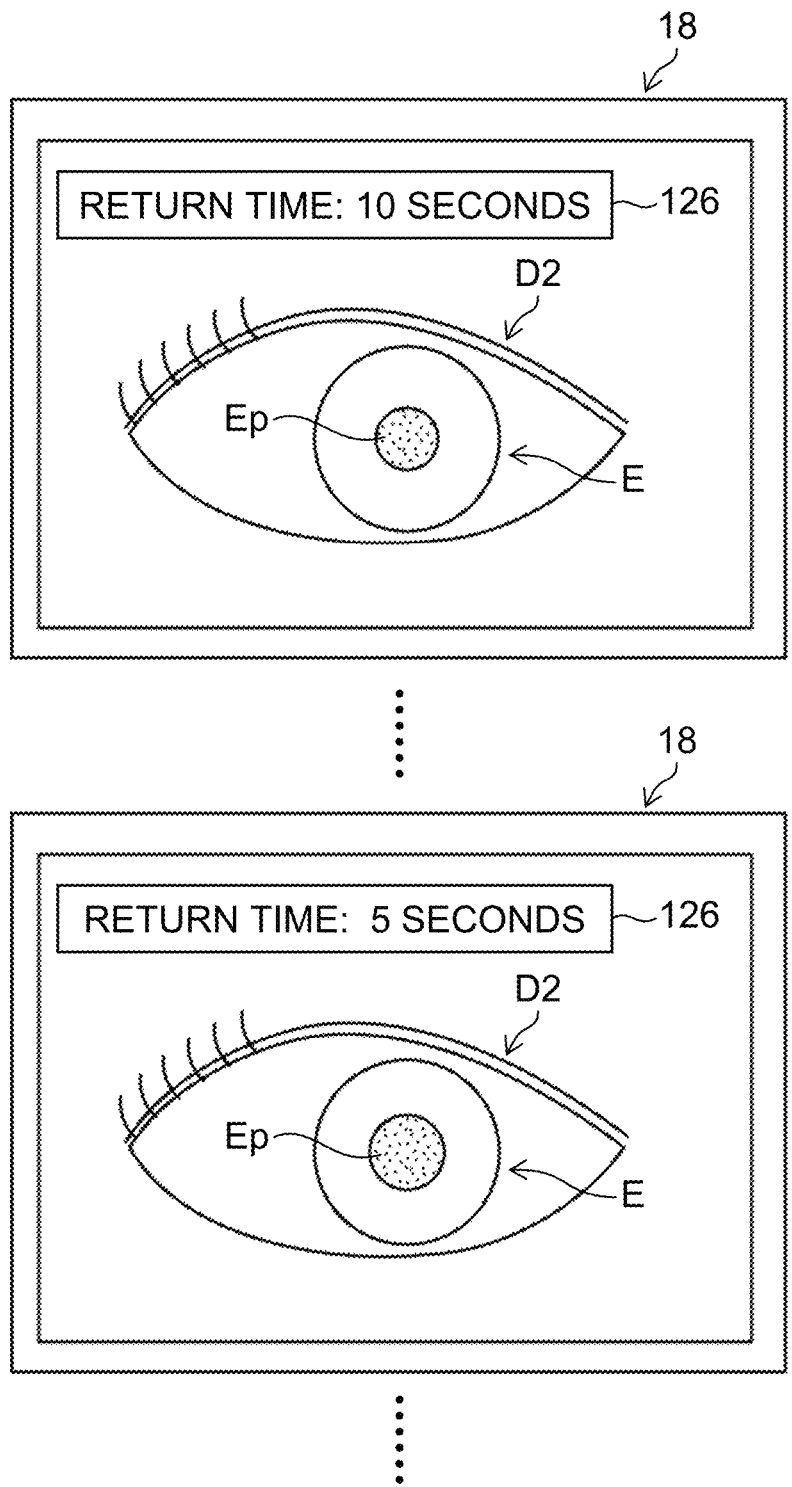
FIG. 15 is an explanatory diagram showing an example of display of return time information on a monitor.

FIG. 15 is an explanatory diagram showing an example of displaying the return time information 126 on the monitor 18. As shown in FIG. 15 and the above-mentioned FIGS. 12 and 13, the notification control unit 112 constitutes a notifying unit of the present invention together with the monitor 18 and the speaker 119. The notification control unit 112 outputs the return time information 126 input from the time predicting unit 110 to the monitor 18 and the speaker 119. As a result, the return time information 126 is displayed on the monitor 18 together with, for example, the anterior ocular segment image D2 (video image). Further, the return time information 126 is output with voice from the speaker 119.

Figure 16:
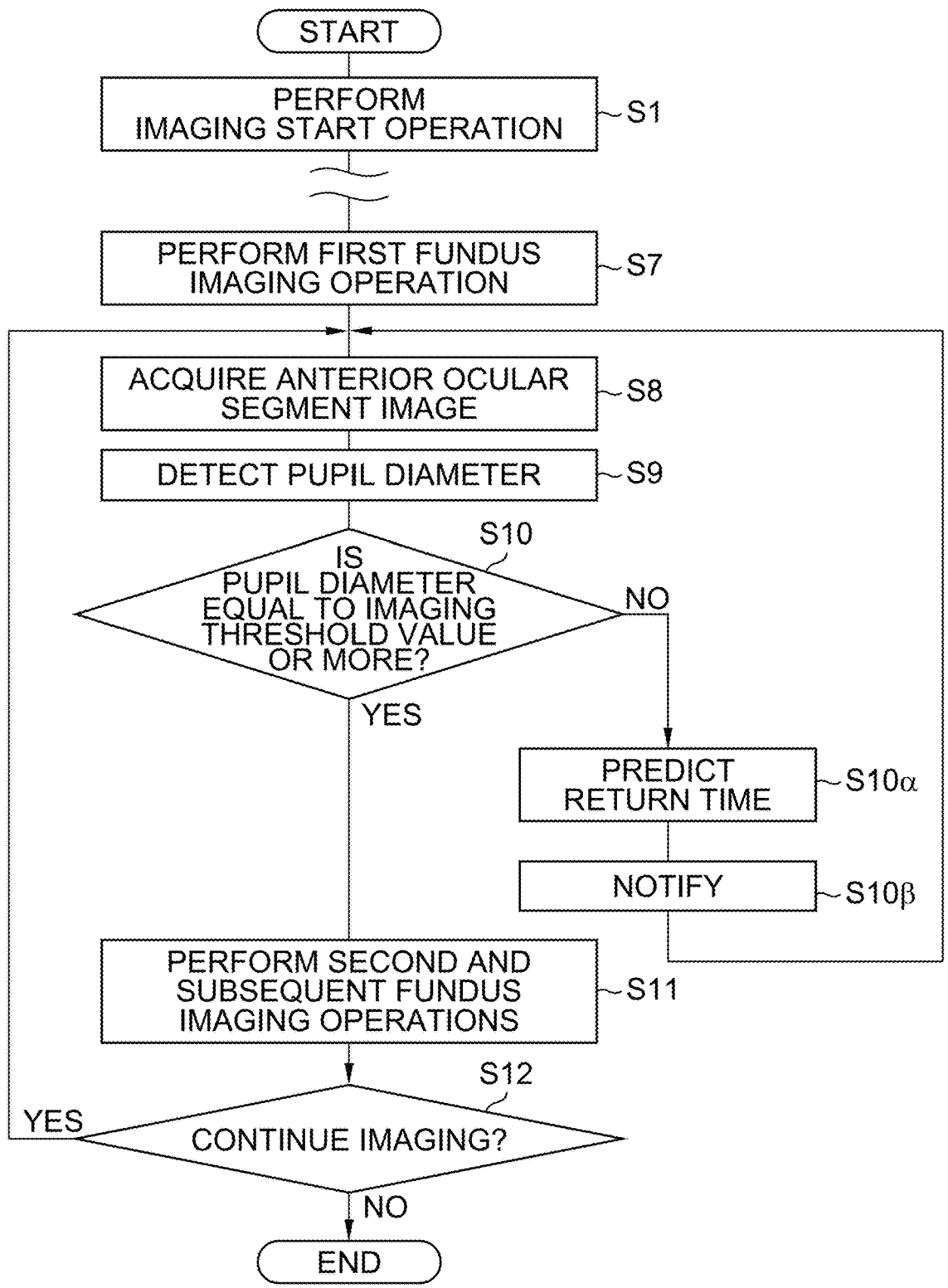
FIG. 16 is a flowchart showing the flow of fundus imaging processing for a subject eye by the ophthalmologic apparatus according to the fourth embodiment.

FIG. 16 is a flowchart showing the flow of the fundus imaging processing on the subject eye E by the ophthalmologic apparatus 10 according to the fourth embodiment. Since the processing from step S1 to step S9 is the same as those of the first embodiment (see FIG. 8) and the second embodiment (see FIG. 12) described above, specific description thereof will be omitted.

As shown in FIG. 16, when the pupil diameter d repeatedly detected by the pupil diameter detecting unit 104 is less than the imaging threshold value T1 after the first fundus imaging operation on the subject eye E by the fundus camera unit 14a is completed (No in step S10), the time predicting unit 110 operates. The time predicting unit 110 predicts the return time t and outputs the return time information 126 to the notification control unit 112 as described with reference to FIG. 13 or FIG. 14, based on the detection result of the pupil diameter detecting unit 104 and the like (step S10α).

The notification control unit 112 outputs the return time information 126 input from the time predicting unit 110 to the monitor 18 and the speaker 119 (step S10β). As a result, as shown in FIG. 15 described above, the return time information 126 is notified from the monitor 18 and the speaker 119 (screen display and voice output).

Hereinafter, the processing of steps S8 to S10, S10α, and S10β is repeatedly executed until the pupil diameter d repeatedly detected by the pupil diameter detecting unit 104 reaches the imaging threshold value T1 or more. As a result, the update of the prediction result of the return time t by the time predicting unit 110 and the notification of the return time information 126 by the notification control unit 112 are repeatedly performed (NO in step S10).

Since the processing to be executed after the pupil diameter d reaches the imaging threshold value T1 or more is the same as that of the first embodiment, the description thereof will be omitted. When the state in which the pupil diameter d is less than the imaging threshold value T1 continues for a certain period of time or more, the fundus imaging on the subject eye E may be performed by using the small pupil diaphragm 39A in the same manner as in the case of the second embodiment.

As described above, in the fourth embodiment, when the second and subsequent fundus imaging operations are performed on the subject eye E, the return time t required until the miosis of the pupil Ep of the subject eye E is settled can be predicted and notified to the operator or the like. As a result, the operator can recognize the return time t, that is, the timings at which the second and subsequent fundus imaging operations on the subject eye E are started.

In the fourth embodiment, the monitor 18 and the speaker 119 are used to notify the return time information 126 (return time t), but only one of the monitor 18 and the speaker 119 may be used to notify the return time information 126.

Fifth Embodiment

Next, an ophthalmologic apparatus 10 according to a fifth embodiment of the present invention will be described. In each of the above-mentioned embodiments, the imaging threshold value T1 is determined based on the pupil diameter d before the first fundus imaging operation on the subject eye E, and the imaging control is executed in the second and subsequent fundus imaging operations based on this imaging threshold value T1. However, in the fifth embodiment, the imaging control is executed from the time when the first fundus imaging operation on the subject eye E is performed.

Note that the ophthalmologic apparatus 10 according to the fifth embodiment has basically the same configuration as the ophthalmologic apparatus 10 of each of the above-mentioned embodiments except that the imaging threshold value T1 is stored in the storage unit 92 in advance. Therefore, components having the same functions or configurations as those of each of the above-mentioned embodiments are designated by the same reference numerals or reference characters, and the description thereof will be omitted.

The imaging threshold value T1 according to the fifth embodiment is, for example, a threshold value determined based on a standard pupil diameter d, or a threshold value which is individually determined for each of various conditions such as the age, disease and the like of the subject. The pupil diameter d of the pupil Ep of each subject may be measured in advance and stored in a database of a hospital or the like, so that the threshold value determining unit 106 accesses the database to acquire information on the pupil diameter d of the subject, determines an imaging threshold value T1 based on thus-acquired information and stores the imaging threshold value T1 in the storage unit 92.

Figure 17:
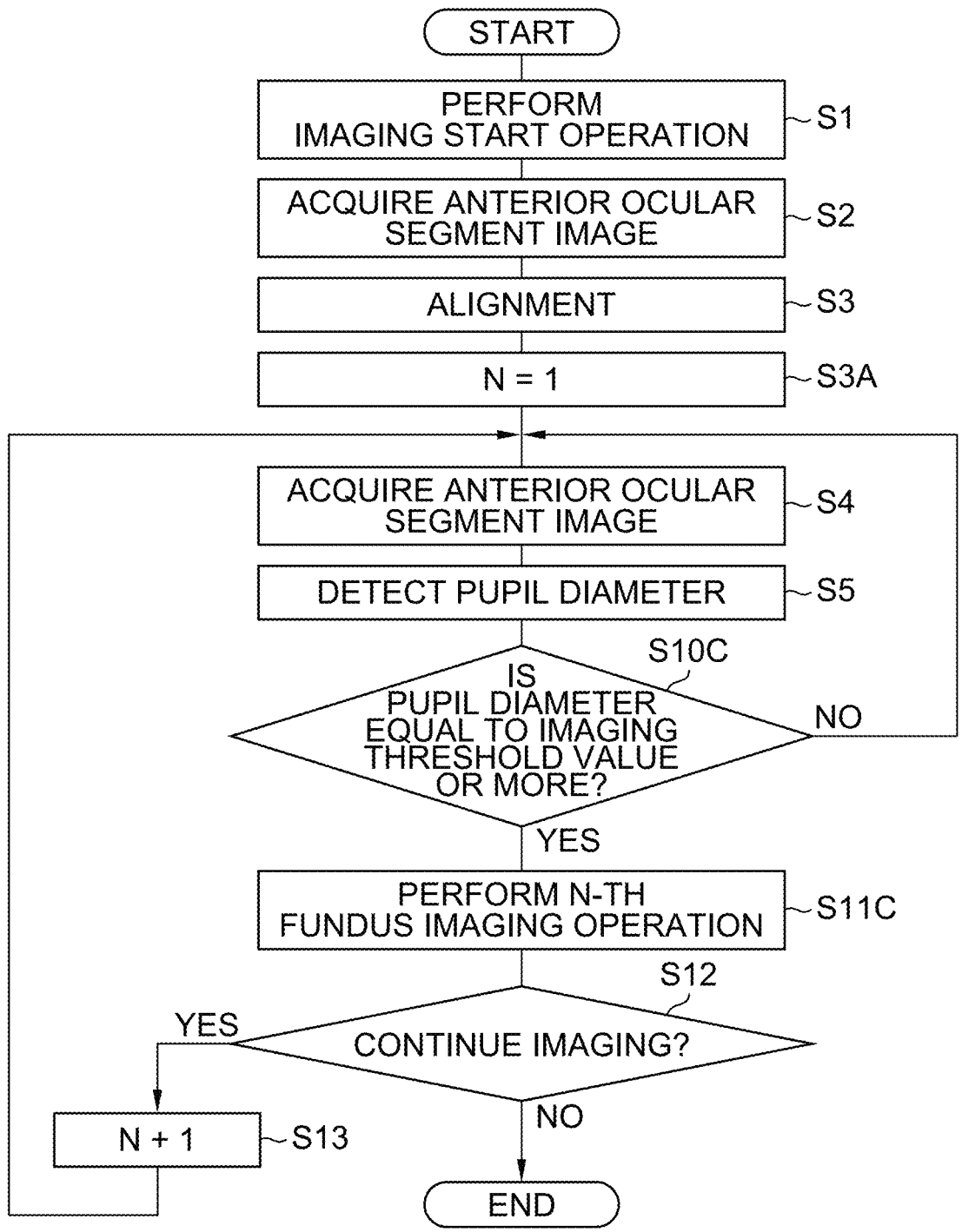
FIG. 17 is a flowchart showing the flow of fundus imaging processing for a subject eye by an ophthalmologic apparatus according to a fifth embodiment.

FIG. 17 is a flowchart showing the flow of fundus imaging processing on the subject eye E by the ophthalmologic apparatus 10 according to the fifth embodiment. Since the processing from step S1 to step S3 is the same as that of the first embodiment described with reference to FIG. 8 described above, specific description thereof will be omitted.

As shown in FIG. 17, the imaging control unit 108 according to the fifth embodiment acquires the imaging threshold value T1 from the storage unit 92 before the first (N=1) fundus imaging operation on the subject eye E (step S3A). When the acquisition of the anterior ocular segment image D2 by the anterior ocular segment image acquiring unit 100 and the detection of the pupil diameter d by the pupil diameter detecting unit 104 are performed (steps S4 and S5), the imaging control unit 108 suspends execution of the first fundus imaging operation on the subject eye E until the pupil diameter d reaches the imaging threshold value T1 or more based on the detection result of the pupil diameter d (NO in step S10C).

When the pupil diameter d repeatedly detected by the pupil diameter detecting unit 104 reaches the imaging threshold value T1 or more, the imaging control unit 108 causes the fundus camera unit 14a to execute the first fundus imaging operation on the subject eye E (YES in step S10C, step S11). As a result, even in a case where miosis has been caused in the pupil Ep because the subject eye E was irradiated with illumination light in another examination or the like before the fundus imaging, the first fundus imaging operation by the fundus camera unit 14a can be automatically performed at a time of the settlement of the miosis. As a result, an excellent fundus image D1 can be obtained.

As in the case of the second embodiment, when the state where the pupil diameter d is less than the imaging threshold value T1 continues for a certain period of time or more, the fundus imaging on the subject eye E may be performed by using the small pupil diaphragm 39A.

Hereinafter, when the second and subsequent (N≥2) fundus imaging operations on the subject eye E are performed, the processing from step S4 to step S11C is repeatedly executed (steps S12 and S13).

As described above, in the ophthalmologic apparatus 10 according to the fifth embodiment, the imaging threshold value T1 is determined in advance, so that the imaging control can be executed from the time when the first fundus imaging operation on the subject eye E is performed. As a result, an excellent fundus image D1 can be obtained even when miosis has been caused in the pupil Ep of the subject eye E due to another examination performed before the fundus imaging.

[Others]

In each of the above-mentioned embodiments, the pupil diameter detecting unit 104 detects the pupil diameter d of the subject eye E based on the anterior ocular segment image D2 captured by the stereo camera 20. However, the pupil diameter d may be detected based on the anterior ocular segment image D2 captured by the fundus camera unit 14a.

Even in this case, it is also possible to perform the imaging control by the imaging control unit 108 described above.

In each of the above-mentioned embodiments, the capture of the anterior ocular segment image D2 by the stereo camera 20 or the fundus camera unit 14a is repeatedly performed (sequentially performed) during the period of time from the time when an imaging start operation is performed until the time when all the fundus imaging operations on the subject eye E are completed. However, the capture of the anterior ocular segment image D2 may be repeatedly performed for only a predetermined period of time before the fundus imaging on the subject eye E.

In each of the above-mentioned embodiments, the diaphragm 39 and the small pupil diaphragm 39A are separately provided. However, a variable diaphragm having an adjustable diaphragm diameter may function as the diaphragm 39 and the small pupil diaphragm 39A.

In each of the above-mentioned embodiments, the composite machine of the fundus camera and the optical coherence tomography meter has been described as an example, but the present invention is also applicable to a fundus camera (non-mydriatic fundus camera) that performs fundus imaging on a subject eye E under non-mydriasis.

DESCRIPTION OF REFERENCE NUMERALS

10: Ophthalmologic apparatus
11: base
12: face supporting part
12a: jaw holder
12b: forehead pad
13: pedestal
14: measuring head
14a: fundus camera unit
14b: OCT unit
15: external fixation lamp
16: operating unit
16a: manipulating lever
17: electric drive mechanism
18: monitor
19: lens accommodating part
20: stereo camera
20a: first camera
20b: second camera
22: arithmetic control unit
30: illumination optical system
31: observation light source
32: reflection mirror
33: condenser lens
34: visible light cut filter
35: imaging light source
36: mirror
37: relay lens
38: relay lens
39: diaphragm
39A: small pupil diaphragm
39B: diaphragm switching mechanism
40: relay lens
41: perforated mirror
42: dichroic mirror
43: objective lens
50: imaging optical system
51: focusing lens
52: mirror
53: half mirror
54: visual target display unit
55: dichroic mirror
56: condenser lens
57: imaging element
58: mirror
59: condenser lens
60: imaging element
70: focus optical system
71: LED
72: relay lens
73: split index plate
74: two-hole diaphragm
75: mirror
76: condenser lens
77: reflective rod
80: OCT optical system
81: collimator lens unit
82: optical path length changing unit
83: Galvano scanner
84: focusing lens
85: mirror
86: relay lens
90: integrated control unit
92: storage unit
94: image forming unit
96: data processing unit
100: anterior ocular segment image acquiring unit
102: alignment control unit
104: pupil diameter detecting unit
106: threshold value determining unit
108: imaging control unit
109: small pupil diameter determining unit
110: time predicting unit
112: notification control unit
119: speaker
120: pupil diameter information
122: light source information
124: subject information
126: return time information
D1: fundus image
D2: anterior ocular segment image
E: subject eye
Ea: anterior ocular segment
Eb: pupillary margin
Ef: fundus
Ep: pupil
Er: iris
MV: actual measurement value
OA: optical axis
PV: prediction value
T1: imaging threshold value
T2: determination threshold value
W: waveform
d: pupil diameter
t: return time

What is claimed is:

1. A fundus camera comprising:
a camera main body configured to image a fundus of a subject eye, wherein the camera main body is configured to perform first imaging on the fundus and second imaging subsequent to the first imaging;
an anterior ocular segment image acquiring circuit configured to repeatedly acquire an anterior ocular segment image of the subject eye at least before the fundus is imaged by the camera main body;
a pupil diameter detecting circuit configured to repeatedly detect a pupil diameter of the subject eye based on the anterior ocular segment image repeatedly acquired by the anterior ocular segment image acquiring circuit;

an imaging control circuit configured to cause the camera main body to image the fundus in a case where the pupil diameter detected by the pupil diameter detecting circuit reaches a predetermined first threshold value or more;

a small pupil diaphragm provided so as to be arrangeable on an optical path of an illumination optical system that is configured to illuminate the fundus with imaging illumination light in a visible wavelength band when the camera main body images the fundus, wherein the small pupil diaphragm is adapted to a small pupil eye; and a first special imaging control circuit configured to cause the camera main body to image the fundus in a state where the small pupil diaphragm is arranged on the optical path when the pupil diameter is less than the first threshold value even after a lapse of a certain predetermined time, based on the pupil diameter repeatedly detected by the pupil diameter detecting circuit after the first imaging and before start of the second imaging.

2. The fundus camera according to claim 1, wherein the camera main body includes the illumination optical system, and the imaging control circuit suspends execution of the second imaging by the camera main body until the pupil diameter reaches the first threshold value or more based on a detection result of the pupil diameter repeatedly detected by the pupil diameter detecting circuit after the first imaging and before start of the second imaging, and causes the camera main body to perform the second imaging when the pupil diameter reaches the first threshold value or more.

3. The fundus camera according to claim 2, further comprising a threshold value determining circuit configured to determine the first threshold value based on the pupil diameter detected by the pupil diameter detecting circuit before the first imaging, wherein the imaging control circuit causes the camera main body to perform the second imaging when the pupil diameter detected by the pupil diameter detecting circuit reaches the first threshold value determined by the threshold value determining circuit or more.

4. The fundus camera according to claim 3, wherein the camera main body performs the first imaging and the second imaging on the same subject eye.

5. The fundus camera according to claim 3, wherein when the subject eye is either of right and left eyes, the camera main body performs the first imaging on one of the right and left eyes, and performs the second imaging on another eye of the right and left eyes.

6. The fundus camera according to claim 2, further comprising:

a time predicting circuit configured to predict a return time required until the pupil diameter increases up to the first threshold value, based on a detection result of the pupil diameter detecting circuit when the camera main body has performed the first imaging; and a notifying circuit configured to notify the return time predicted by the time predicting circuit.

7. The fundus camera according to claim 6, wherein the time predicting circuit predicts the return time based on the detection result by the pupil diameter detecting circuit and a type of the imaging illumination light.

8. The fundus camera according to claim 6, wherein the time predicting circuit detects a change in the pupil diameter after the first imaging is performed based on the pupil diameter repeatedly detected by the pupil diameter detecting circuit, and calculates the return time based on a detection result of the change in the pupil diameter.

9. The fundus camera according to claim 1, wherein the camera main body includes an illumination optical system configured to illuminate the fundus with imaging illumination light in a visible wavelength band, and the fundus camera further comprises:

a small pupil diameter determining circuit configured to determine based on a detection result by the pupil diameter detecting circuit, whether the subject eye is a small pupil eye;

a small pupil diaphragm provided so as to be arrangeable on an optical path of the illumination optical system and adapted to the small pupil eye; and a second special imaging control circuit configured to cause the camera main body to image the fundus in a state where the small pupil diaphragm is arranged on the optical path in a case where the small pupil diameter determining circuit determines that the subject eye is the small pupil eye.

10. The fundus camera according to claim 9, wherein the small pupil diameter determining circuit determines whether the subject eye is a small pupil eye based on whether the pupil diameter detected by the pupil diameter detecting circuit is less than a predetermined second threshold value which is smaller than the first threshold value.

11. A control method of a fundus camera for imaging a fundus of a subject eye, comprising:

an anterior ocular segment image acquiring step of repeatedly acquiring an anterior ocular segment image of the subject eye at least before the fundus is imaged;

a pupil diameter detecting step of repeatedly detecting a pupil diameter of the subject eye based on the anterior ocular segment image that is repeatedly acquired in the anterior ocular segment image acquiring step;

an imaging control step of imaging the fundus when the pupil diameter detected in the pupil diameter detecting step reaches a predetermined first threshold value or more; and a first special imaging control step of imaging the fundus in a state where a small pupil diaphragm is arranged on an optical path of illumination light in a visible wavelength band for illuminating the fundus when the pupil diameter is less than the first threshold value even after a lapse of a certain predetermined time, based on the pupil diameter repeatedly detected by the pupil diameter detecting circuit after the first imaging and before start of the second imaging.

* * * * *